United States Patent
Janagani et al.

(10) Patent No.: US 9,938,282 B2
(45) Date of Patent: Apr. 10, 2018

(54) EXPEDIENT SYNTHESIS OF SITAGLIPTIN

(71) Applicant: STEREOKEM, INC., Santa Clara, CA (US)

(72) Inventors: Satyanarayana Janagani, Santa Clara, CA (US); Venkateshwar Kumar Thaduri, Hyderabad (IN); Ravisankar Vamaraju, Hyderabad (IN)

(73) Assignee: STEREOKEM, INC., Santa Clara, CA (US)

( * ) Notice: Subject to any disclaimer, the term of this patent is extended or adjusted under 35 U.S.C. 154(b) by 0 days.

(21) Appl. No.: 15/117,097

(22) PCT Filed: Feb. 5, 2015

(86) PCT No.: PCT/US2015/014548
§ 371 (c)(1),
(2) Date: Aug. 5, 2016

(87) PCT Pub. No.: WO2015/120111
PCT Pub. Date: Aug. 13, 2015

(65) Prior Publication Data
US 2017/0183351 A1   Jun. 29, 2017

Related U.S. Application Data

(60) Provisional application No. 61/936,291, filed on Feb. 5, 2014.

(51) Int. Cl.
*C07D 487/04*   (2006.01)
*C07D 487/00*   (2006.01)

(52) U.S. Cl.
CPC .......... *C07D 487/04* (2013.01); *C07D 487/00* (2013.01)

(58) Field of Classification Search
CPC .................................................. C07D 487/04
See application file for complete search history.

*Primary Examiner* — Brian E McDowell
(74) *Attorney, Agent, or Firm* — Klauber & Jackson LLC

(57) ABSTRACT

Novel intermediates are disclosed as intermediates for preparation of a Sitagliptin. A novel synthetic method to prepare Sitagliptin using the said intermediates is also disclosed.

7 Claims, No Drawings

EXPEDIENT SYNTHESIS OF SITAGLIPTIN

PRIORITY

The present application is the National Stage Application which claims priority of co-pending PCT Application No. PCT/US2015/014548, filed Feb. 5,2015, which in turn claims priority from U.S. Provisional Application Ser. No. 61/936,291, entitled "Expedient synthesis of Sitagliptin" and filed on Feb. 5, 2014. Applicants claim the benefits of 35 U.S.C. § 120 as to the PCT application and priority under 35 U.S.C. § 119 as to said U.S. provisional application, and the entire disclosures of all applications are incorporated herein by reference in their entireties.

FIELD OF THE INVENTION

The present invention provides novel intermediates and their use in the preparation of (R)-3-amino-1-(3-trifluoromethyl-5,6-dihydro-8H-[1,2,4]triazolo[4,3-a]pyrazin-7-yl)-4-(2,4,5-trifluoro-phenyl)-butan-1-one (Sitagliptin). Furthermore, the present invention provides processes for the preparation of Sitagliptin and related compounds useful, for example, in Type II diabetes therapy.

BACKGROUND OF THE INVENTION ((R)-3-amino-1-(3-trifluoromethyl-5,6-dihydro-8H-[1,2,4]triazolo[4,3-a]pyrazin-7-yl)-4-(2,4,5-trifluoro-phenyl)-butan-1-one, is a dipeptidyl peptidase-4 (DPP-IV) enzyme modulator and is useful in Type 2 diabetes therapy. The compound is also known as Sitagliptin. Sitagliptin also exists as its acid salts. The salt of sitagliptin has the following chemical structure:

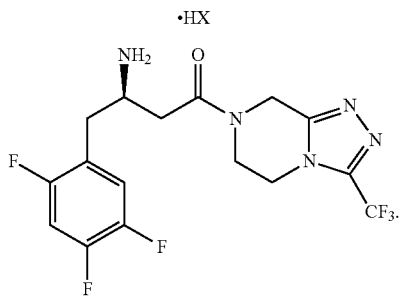

IV

The phosphate salt of sitagliptin has the following chemical structure:

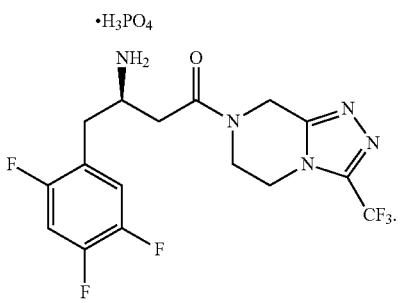

IV'

In a specific embodiment, sitagliptin is a monohydrate of the phosphate salt of sitagliptin, and has the following chemical structure:

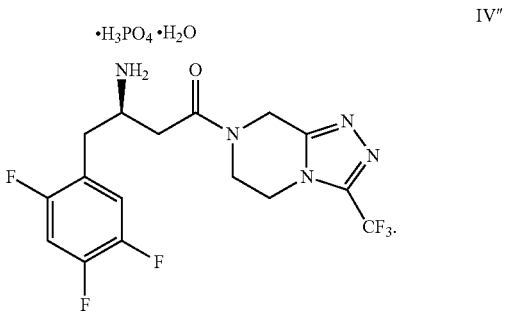

IV''

Sitagliptin is used either alone or in combination with other oral antihyperglycemic agents (such as metformin or a thiazolidinedione) for treatment of diabetes mellitus type II. The benefit of this medicine is its lower side-effects (e.g., less hypoglycemia, less weight gain) in the control of blood glucose values.

Sitagliptin works to competitively inhibit the enzyme dipeptidyl peptidase 4 (DPP-4). This enzyme breaks down the incretins GLP-1 and GIP, gastrointestinal hormones that are released in response to a meal (*J Clin Pharmacol* 46 (8): 876-86). By preventing GLP-1 and GIP inactivation, GLP-1 and GIP are able to potentiate the secretion of insulin and suppress the release of glucagon by the pancreas. This drives blood glucose levels towards normal. As the blood glucose level approaches normal, the amounts of insulin released and glucagon suppressed diminish, thus tending to prevent an "overshoot" and subsequent low blood sugar (hypoglycemia) that is seen with some other oral hypoglycemic agents (Wikipedia).

International Application Publication No. WO2003/004498 and U.S. Pat. No. 6,699,871, describe the use of sitagliptin and analogs, and the composition thereof.

Several processes for the synthesis of sitagliptin are known. For example, International Application Publication WO2004/085661 discloses the preparation of sitagliptin using S-phenylglycine amide as a chiral auxiliary.

International Application Publication No. WO2004/087650 discloses the preparation of sitagliptin using the chiral benzyloxylazetidinone as an intermediate.

International Application Publication Nos. WO2004/085378, WO2005/097733, and WO2006/081151 disclose the preparation of sitagliptin which involves an enantioselective reduction of the intermediate chiral enamine in the presence of specific catalysts.

International Application Publication No. WO2009/085990 discloses the preparation of sitagliptin using various chiral auxiliaries, such as chiral resolving agents.

While these methods are useful for preparing Sitagliptin, alternative methods of the preparation, particularly for manufacturing scale production, are desirable.

Citation of any reference in this application is not to be construed as an admission that such reference is prior art to the present application.

SUMMARY OF THE INVENTION

Novel intermediates, and use thereof, in the preparation of Sitagliptin are described herein.

Accordingly, in one aspect of the invention, the novel intermediates are provided as useful synthons for preparation of Sitagliptin and pharmaceutically acceptable salt thereof.

In particular aspects, the present invention provides processes for the preparation of an intermediate compound of formula I:

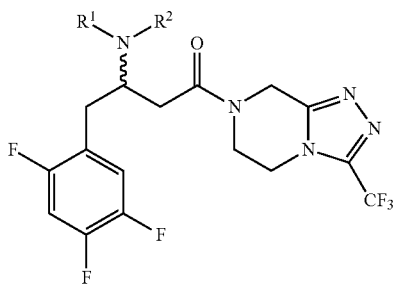

I or a salt thereof; wherein each $R^1$ and $R^2$ is independently H, substituted or unsubstituted alkyl, substituted or unsubstituted alkoxy, substituted or unsubstituted aryl, substituted or unsubstituted aryloxy, substituted or unsubstituted aralkyl, substituted or unsubstituted heterocycloalkyl, or substituted or unsubstituted cycloalkyl, —C(O)—$R^3$, —C(O)—O$R^3$, —O—C(O)—$R^3$, —S(O)$_2$—$R^3$, —Si($R^3$)$_3$, and —O—Si($R^3$)$_3$; each $R^3$ is independently selected from substituted or unsubstituted alkyl, substituted or unsubstituted benzyl, substituted or unsubstituted cycloalkyl, substituted or unsubstituted aryl, and substituted or unsubstituted heteroaryl;

or $R^1$ and $R^2$ are joined together to form a heterocycle; and the wavy bond represents that the compound is in R—, S— or racemic form;

wherein the process comprises the steps of:

A1) providing an intermediate compound of formula II:

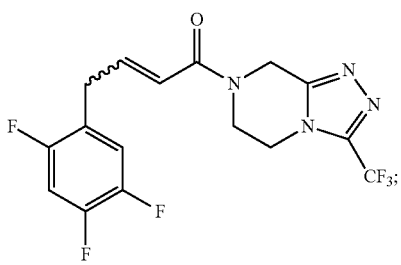

II

A2) reacting the intermediate compound of formula II with a Michael donor of formula III:

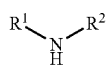

III wherein $R^1$ and $R^2$ are as described above;

to obtain the intermediate compound of formula I.

In another aspect, the present invention provides stereoselective processes for the preparation of a pharmaceutically acceptable salt of sitagliptin of the formula IV:

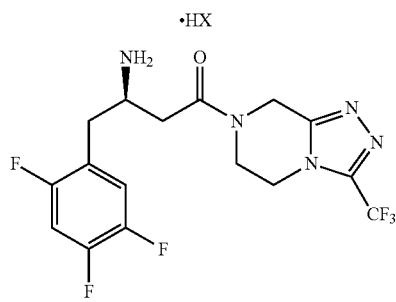

IV or a solvate, or polymorph thereof; wherein HX is a pharmaceutically acceptable acid; comprising the steps of:

B1) reacting the compound of formula II or an isomer thereof:

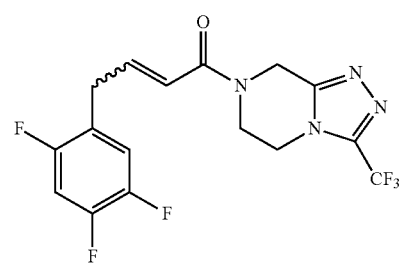

II with a Michael donor of formula III:

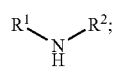

III wherein each $R^1$ and $R^2$ is H; or $R^1$ is H, and $R^2$ is t-butyl, 1,1,1-triphenylmethyl, or —C(O)—O-t-Bu;

to form a mixture of isomers according to formula Va and Vb:

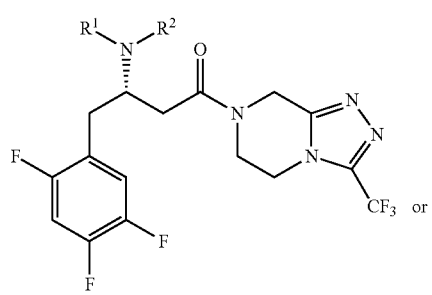

Va or

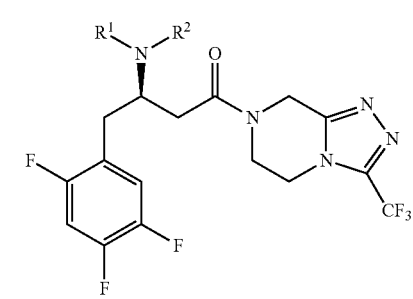

Vb

B2) separating the compound of formula Vb from the mixture of isomers;

B3) reacting the compound of formula Vb with HX to produce the pharmaceutically acceptable salt of sitagliptin of the formula IV or a solvate, or polymorph thereof.

In one embodiment, $R^1$ and $R^2$ are as described in the context of formula I.

In yet another aspect, the present invention provides stereoselective process for the preparation of a pharmaceutically acceptable salt of sitagliptin of the formula IV:

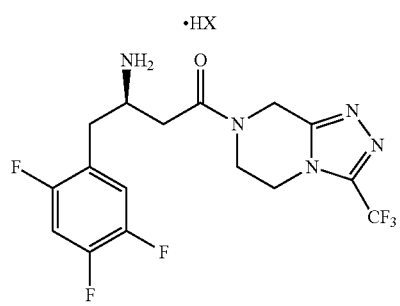

IV or a solvate, or polymorph thereof; wherein HX is a pharmaceutically acceptable acid; comprising the steps of:
C1) reacting the compound of formula II or an isomer thereof:

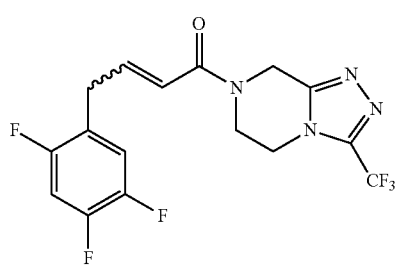

II with a Michael donor of formula III:

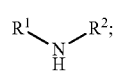

III wherein $R^1$ is H, and $R^2$ is substituted or unsubstituted benzyl, —C(O)O-benzyl, CH(Me)-Ph, —CH(Me)-naphth-2-yl, or —CH(Ph)-C(O)OR$^{4a}$, —CH(Ph)-C(O)NR$^{4a}$R$^{4b}$; each R$^{4a}$ and R$^{4b}$ is independently H, substituted or unsubstituted alkyl, benzyl, or substituted or unsubstituted cycloalkyl; or $R^1$ and $R^2$ are joined together to form a heterocycle; and Ph is substituted or unsubstituted phenyl; to form a mixture of isomers according to formula Va and Vb:

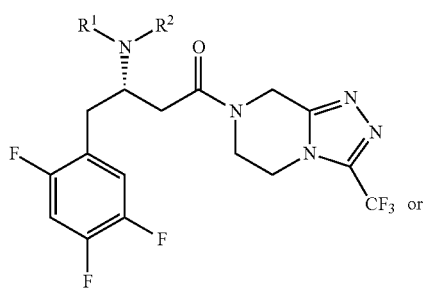

Va or

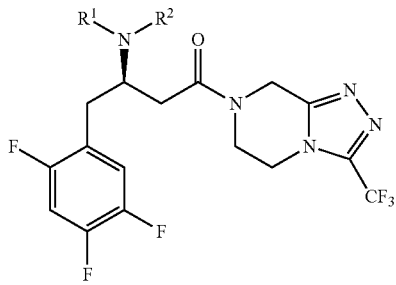

Vb

C2) separating the compound of formula Vb from the mixture of isomers;
C3) reacting the compound of formula Vb with HX to obtain the salt of formula VI:

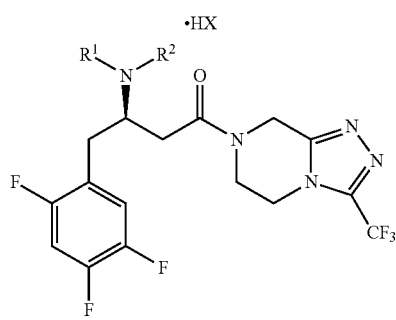

VI

C4) hydrogenolysis of the compound of formula VI or a solvate or polymorph, thereof; to produce the pharmaceutically acceptable salt of sitagliptin of the formula IV or a solvate, or polymorph thereof.

In a particular aspect, the present invention provides compounds according to formula XI:

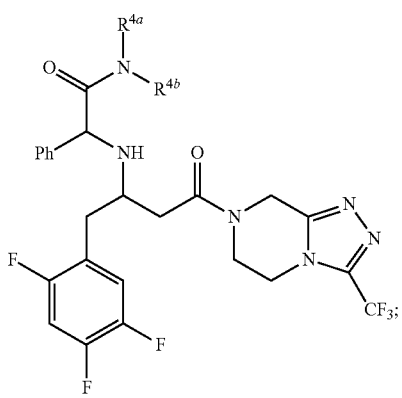

XI or a solvate, polymorph, pharmaceutically acceptable salt or isomer thereof;
wherein
each R$^{4a}$ and R$^{4b}$ is independently H, substituted or unsubstituted alkyl, benzyl, or substituted or unsubstituted cycloalkyl; or R$^{4a}$ and R$^{4b}$ are joined together to form a heterocycle; Ph is substituted or unsubstituted phenyl; provided that when each of R$^{4a}$ and R$^{4b}$ is H; then the compound is in a form of an acid addition salt.

In another particular aspect, the present invention provides compounds according to formula XVIa or XVIb:

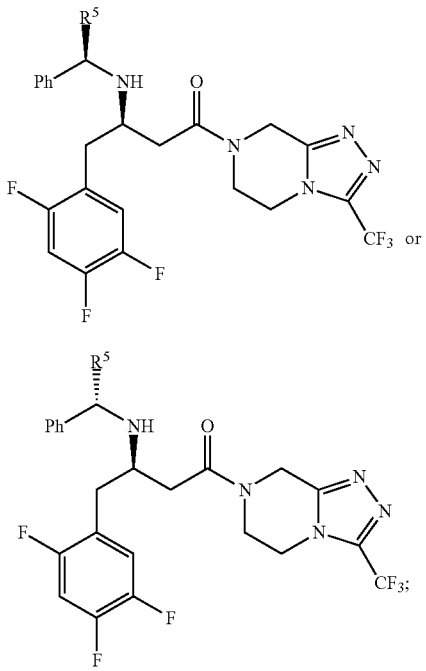

or a solvate, polymorph, pharmaceutically acceptable salt or isomer thereof;

Ph is substituted or unsubstituted phenyl, $R^5$ is substituted methyl, substituted or unsubstituted C2-C6 alkyl, or —COOR$^{4a}$; and R$^{4a}$, is as described for formula XI; or Ph is substituted phenyl, and $R^5$ is Me.

In additional aspects, methods are provided for synthesizing the compounds described herein, with representative synthetic protocols and pathways described herein.

Other objects and advantages will become apparent to those skilled in the art from a consideration of the ensuing detailed description.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Acyl' or 'Alkanoyl' refers to a radical —C(O)R$^{20}$, where R$^{20}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocycloalkyl), wherein t is an integer from 0 to 4.

'Substituted Acyl' or 'Substituted Alkanoyl' refers to a radical —C(O)R$^{21}$, wherein R$^{21}$ is independently
$C_1$-$C_8$ alkyl, substituted with halo or hydroxy; or
$C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Acylamino' refers to a radical —NR$^{22}$C(O)R$^{23}$, where R$^{22}$ is hydrogen, $C_1$-$C_8$ alkyl, $C_3$-$C_{10}$ cycloalkyl, 4-10 membered heterocycloalkyl, $C_6$-$C_{10}$ aryl, arylalkyl, 5-10 memberd heteroaryl or heteroarylalkyl and R$^{23}$ is hydrogen, $C_1$-$C_8$ alkyl, $C_3$-$C_{10}$ cycloalkyl, 4-10 membered heterocycloalkyl, $C_6$-$C_{10}$ aryl, arylalkyl, 5-10 membered heteroaryl or heteroarylalkyl, as defined herein. Exemplary 'acylamino' include, but are not limited to, formylamino, acetylamino, cyclohexylcarbonylamino, cyclohexylmethyl-carbonylamino, benzoylamino and benzylcarbonylamino. Particular exemplary 'acylamino' groups are —NR$^{24}$C(O)—$C_1$-$C_8$ alkyl, —NR$^{24}$C(O)—(CH$_2$)$_t$(C$_6$-$C_{10}$ aryl), —NR$^{24}$C(O)—(CH$_2$)$_t$(5-10 membered heteroaryl), —NR$^{24}$C(O)—(CH$_2$)$_t$(C$_3$-$C_{10}$ cycloalkyl), and —NR$^{24}$C(O)—(CH$_2$)$_t$(4-10 membered heterocycloalkyl), wherein t is an integer from 0 to 4, and each R$^{24}$ independently represents H or $C_1$-$C_8$ alkyl.

'Substituted Acylamino' refers to a radical —NR$^{25}$C(O)R$^{26}$, wherein:
R$^{25}$ is independently
H, $C_1$-$C_8$ alkyl, substituted with halo or hydroxy; or
$C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and
R$^{26}$ is independently
—H, $C_1$-$C_8$ alkyl, substituted with halo or hydroxy; or
—$C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl;
provided at least one of R$^{25}$ and R$^{26}$ is other than H.

'Acyloxy' refers to a radical —OC(O)R$^{27}$, where R$^{27}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—$(CH_2)_t$($C_6$-$C_{10}$ aryl), —C(O)—$(CH_2)_t$(5-10 membered heteroaryl), —C(O)—$(CH_2)_t$($C_3$-$C_{10}$ cycloalkyl), and —C(O)—$(CH_2)_t$(4-10 membered heterocycloalkyl), wherein t is an integer from 0 to 4.

'Substituted Acyloxy' refers to a radical —OC(O)$R^{28}$, wherein $R^{28}$ is independently $C_1$-$C_8$ alkyl, substituted with halo or hydroxy; or $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkoxy' refers to the group —$OR^{29}$ where $R^{29}$ is $C_1$-$C_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocycloalkyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups are —O—$(CH_2)_t$($C_6$-$C_{10}$ aryl), —O—$(CH_2)_t$(5-10 membered heteroaryl), —O—$(CH_2)_t$($C_3$-$C_{10}$ cycloalkyl), and —O—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are $OCF_3$, $OCH_2CF_3$, $OCH_2Ph$, $OCH_2$—cyclopropyl, $OCH_2CH_2OH$, and $OCH_2CH_2NMe_2$.

'Alkoxycarbonyl' refers to a radical —C(O)—$OR^{30}$ where $R^{30}$ represents an $C_1$-$C_8$ alkyl, $C_3$-$C_{10}$ cycloalkyl, $C_3$-$C_{10}$ cycloalkylalkyl, 4-10 membered heterocycloalkylalkyl, aralkyl, or 5-10 membered heteroarylalkyl as defined herein. Exemplary "alkoxycarbonyl" groups are C(O)O—$C_1$-$C_8$ alkyl, —C(O)O—$(CH_2)_t$($C_6$-$C_{10}$ aryl), —C(O)O—$(CH_2)_t$(5-10 membered heteroaryl), —C(O)O—$(CH_2)_t$($C_3$-$C_{10}$ cycloalkyl), and —C(O)O—$(CH_2)_t$(4-10 membered heterocycloalkyl), wherein t is an integer from 1 to 4.

'Substituted Alkoxycarbonyl' refers to a radical —C(O)—$OR^{31}$ where $R^{31}$ represents:

$C_1$-$C_8$ alkyl, $C_3$-$C_{10}$ cycloalkyl, $C_3$-$C_{10}$ cycloalkylalkyl, or 4-10 membered heterocycloalkylalkyl, each of which is substituted with halo, substituted or unsubstituted amino, or hydroxy; or $C_6$-$C_{10}$ aralkyl, or 5-10 membered heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Aryloxycarbonyl' refers to a radical —C(O)—$OR^{32}$ where $R^{32}$ represents an $C_6$-$C_{10}$ aryl, as defined herein. Exemplary "aryloxycarbonyl" groups is —C(O)O—($C_6$-$C_{10}$ aryl).

'Substituted Aryloxycarbonyl' refers to a radical —C(O)—$OR^{33}$ where $R^{33}$ represents $C_6$-$C_{10}$ aryl, substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Heteroaryloxycarbonyl' refers to a radical —C(O)—$OR^{34}$ where $R^{34}$ represents a 5-10 membered heteroaryl, as defined herein. An exemplary "aryloxycarbonyl" group is —C(O)O-(5-10 membered heteroaryl).

'Substituted Heteroaryloxycarbonyl' refers to a radical —C(O)—$OR^{35}$ where $R^{35}$ represents:

5-10 membered heteroaryl, substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Alkoxycarbonylamino' refers to the group —$NR^{36}$C(O)$OR^{37}$, where $R^{36}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein, and $R^{37}$ is $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein.

'Alkyl' means straight or branched aliphatic hydrocarbon having 1 to 20 carbon atoms. Particular alkyl has 1 to 12 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and iso-amyl.

'Substituted alkyl' refers to an alkyl group as defined above substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)$R^{20}$), alkoxy, alkoxycarbonyl, alkoxycarbonylamino (—NR"-alkoxycarbonyl or —NH—C(O)—$OR^{27}$), amino, substituted amino, aminocarbonyl (carbamoyl or amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, aryloxy, azido, carboxyl, cyano, cycloalkyl, halogen, hydroxy, heteroaryl, nitro, thiol, —S-alkyl, —S-aryl, —S(O)-alkyl, —S(O)-aryl, —S(O)$_2$-alkyl, and —S(O)$_2$-aryl. In a particular embodiment 'substituted alkyl' refers to a $C_1$-$C_8$ alkyl group substituted with halo, cyano, nitro, trifluoromethyl, trifluoromethoxy, azido, —NR'''SO$_2$R", —SO$_2$NR"R''', —C(O)R", —C(O)OR", —OC(O)R", —NR'''C(O)R", —C(O)NR"R''', —NR"R''', or —(CR'''R'''')$_m$OR'''; wherein each R" is independently selected from H, $C_1$-$C_8$ alkyl, —$(CH_2)_t$($C_6$-$C_{10}$ aryl), —$(CH_2)_t$(5-10 membered heteroaryl), —$(CH_2)_t$($C_3$-$C_{10}$ cycloalkyl), and —$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Each of R'" and R"" independently represents H or $C_1$-$C_8$ alkyl.

'Alkylene' refers to divalent saturated alkene radical groups having 1 to 11 carbon atoms and more particularly 1 to 6 carbon atoms which can be straight-chained or branched. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

'Substituted alkylene' refers to those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Alkenyl' refers to monovalent olefinically unsaturated hydrocarbyl groups preferably having 2 to 11 carbon atoms, particularly from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=$CH_2$), n-propenyl (—$CH_2$CH=$CH_2$), isopropenyl (—C($CH_3$)=$CH_2$), vinyl and substituted vinyl, and the like.

'Substituted alkenyl' refers to those groups recited in the definition of 'substituted' herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Alkenylene' refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

'Alkynyl' refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—$CH_2$C≡CH), and the like.

'Substituted alkynyl' refers to those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Amino' refers to the radical —$NH_2$.

'Substituted amino' refers to an amino group substituted with one or more of those groups recited in the definition of 'substituted' herein, and particularly refers to the group —N($R^{38}$)$_2$ where each $R^{38}$ is independently selected from:
  hydrogen, $C_1$-$C_8$ alkyl, $C_6$-$C_{10}$ aryl, 5-10 membered heteroaryl, 4-10 membered heterocycloalkyl, or $C_3$-$C_{10}$ cycloalkyl; or
  $C_1$-$C_8$ alkyl, substituted with halo or hydroxy; or
  —(CH$_2$)$_t$(C$_6$-$C_{10}$ aryl), —(CH$_2$)$_t$(5-10 membered heteroaryl), —(CH$_2$)$_t$(C$_3$-$C_{10}$ cycloalkyl) or —(CH$_2$)$_t$(4-10 membered heterocycloalkyl) wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or
  both $R^{38}$ groups are joined to form an alkylene group.

When both $R^{38}$ groups are hydrogen, —N($R^{38}$)$_2$ is an amino group. Exemplary 'substituted amino' groups are —NR$^{39}$—$C_1$-$C_8$ alkyl, —NR$^{39}$—(CH$_2$)$_t$(C$_6$-$C_{10}$ aryl), —NR$^{39}$—(CH$_2$)$_t$(5-10 membered heteroaryl), —NR$^{39}$—(CH$_2$)$_t$(C$_3$-$C_{10}$ cycloalkyl), and —NR$^{39}$—(CH$_2$)$_t$(4-10 membered heterocycloalkyl), wherein t is an integer from 0 to 4, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term "substituted amino" includes the groups alkylamino, substituted alkylamino, alkylarylamino, substituted alkylarylamino, arylamino, substituted arylamino, dialkylamino and substituted dialkylamino as defined below.

'Alkylamino' refers to the group —NHR$^{40}$, wherein R$^{40}$ is $C_1$-$C_8$ alkyl;

'Substituted Alkylamino' refers to the group —NHR$^{41}$, wherein R$^{41}$ is $C_1$-$C_8$ alkyl; and the alkyl group is substituted with halo, substituted or unsubstituted amino, hydroxy, $C_3$-$C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkylarylamino' refers to the group —NR$^{42}$R$^{43}$, wherein R$^{42}$ is aryl and R$^{43}$ is $C_1$-$C_8$ alkyl.

'Substituted Alkylarylamino' refers to the group —NR$^{44}$R$^{45}$, wherein R$^{44}$ is aryl and R$^{45}$ is $C_1$-$C_8$ alkyl; and the alkyl group is substituted with halo, substituted or unsubstituted amino, hydroxy, $C_3$-$C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Arylamino' means a radical —NHR$^{46}$ where R$^{46}$ is selected from C$_6$-C$_{10}$ aryl and 5-10 membered heteroaryl as defined herein.

'Substituted Arylamino' refers to the group —NHR$^{47}$, wherein R$^{47}$ is independently selected from C$_6$-C$_{10}$ aryl and 5-10 membered heteroaryl; and any aryl or heteroaryl groups present, may themselves be substituted by unsubstituted C$_1$-C$_4$ alkyl, halo, cyano, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Dialkylamino' refers to the group —NR$^{48}$R$^{49}$, wherein each of R$^{48}$ and R$^{49}$ are independently selected from C$_1$-C$_8$ alkyl.

'Substituted Dialkylamino' refers to the group —NR$^{50}$R$^{51}$, wherein each of R$^{59}$ and R$^{51}$ are independently selected from C$_1$-C$_8$ alkyl; and at least one of the alkyl groups is independently substituted with halo, hydroxy, C$_3$-C$_{10}$ cycloalkyl, 4-10 membered heterocycloalkyl, C$_6$-C$_{10}$ aryl, 5-10 membered heteroaryl, aralkyl or heteroaralkyl; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_{1-4}$ haloalkyl, unsubstituted C$_1$-C$_4$ hydroxyalkyl, or unsubstituted C$_1$-C$_4$ haloalkoxy or hydroxy.

'Diarylamino' refers to the group —NR$^{52}$R$^{53}$, wherein each of R$^{52}$ and R$^{53}$ are independently selected from C$_6$-C$_{10}$ aryl.

'Aminosulfonyl' or 'Sulfonamide' refers to the radical —S(O$_2$)NH$_2$.

'Substituted aminosulfonyl' or 'substituted sulfonamide' refers to a radical such as —S(O$_2$)N(R$^{54}$)$_2$ wherein each R$^{548}$ is independently selected from:
  H, C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or
  C$_1$-C$_8$ alkyl substituted with halo or hydroxy; or
  C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy;
provided that at least one R$^{54}$ is other than H.

Exemplary 'substituted aminosulfonyl' or 'substituted sulfonamide' groups are —S(O$_2$)N(R$^{55}$)—C$_1$-C$_8$ alkyl, —S(O$_2$)N(R$^{55}$)—(CH$_2$)$_t$(C$_6$-C$_{10}$ aryl), —S(O$_2$)N(R$^{55}$)—(CH$_2$)$_t$(5-10 membered heteroaryl), —S(O$_2$)N(R$^{55}$)—(CH$_2$)$_t$(C$_3$-C$_{10}$ cycloalkyl), and —S(O$_2$)N(R$^{55}$)—(CH$_2$)$_t$(4-10 membered heterocycloalkyl), wherein t is an integer from 0 to 4; each R$^{55}$ independently represents H or C$_1$-C$_8$ alkyl; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Substituted Aralkyl' or 'substituted arylalkyl' refers to an alkyl group, as defined above, substituted with one or more aryl groups; and at least one of the aryl groups present, may themselves be substituted by unsubstituted C$_1$-C$_4$ alkyl, halo, cyano, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or poly-cyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted Aryl' refers to an aryl group substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

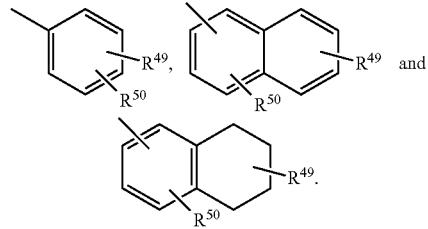

In these formulae one of R$^{56}$ and R$^{57}$ may be hydrogen and at least one of R$^{56}$ and R$^{57}$ is each independently selected from C$_1$-C$_8$ alkyl, C$_1$-C$_8$ haloalkyl, 4-10 membered heterocycloalkyl, alkanoyl, C$_1$-C$_8$ alkoxy, heteroaryloxy, alkylamino, arylamino, heteroarylamino, NR$^{58}$COR$^{59}$, NR$^{58}$SOR$^{59}$, NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O or S. R$^{60}$, and R$^{61}$ are independently hydrogen, C$_1$-C$_8$ alkyl, C$_1$-C$_4$ haloalkyl, C$_3$-C$_{10}$ cycloalkyl, 4-10 membered heterocycloalkyl, C$_6$-C$_{10}$ aryl, substituted aryl, 5-10 membered heteroaryl.

'Fused Aryl' refers to an aryl having two of its ring carbon in common with a second aryl ring or with an aliphatic ring.

'Arylalkyloxy' refers to an —O-alkylaryl radical where alkylaryl is as defined herein.

'Substituted Arylalkyloxy' refers to an —O-alkylaryl radical where alkylaryl is as defined herein; and any aryl groups present, may themselves be substituted by unsubstituted C$_1$-C$_4$ alkyl, halo, cyano, unsubstituted C$_1$-C$_4$ alkoxy, unsubstituted $C_{1-4}$ haloalkyl, unsubstituted $C_1$-$C_4$ hydroxyalkyl, or unsubstituted $C_1$-$C_4$ haloalkoxy or hydroxy.

'Azido' refers to the radical —$N_3$.

'Carbamoyl or amido' refers to the radical —$C(O)NH_2$.

'Substituted Carbamoyl or substituted amido' refers to the radical —$C(O)N(R^{62})_2$ wherein each $R^{62}$ is independently H, $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy;

provided that at least one $R^{62}$ is other than H.

Exemplary 'Substituted Carbamoyl' groups are —$C(O)NR^{64}$—$C_1$-$C_8$ alkyl, —$C(O)NR^{64}$—$(CH_2)_t(C_6$-$C_{10}$ aryl), —$C(O)N^{64}$—$(CH_2)_t(5$-10 membered heteroaryl), —$C(O)NR^{64}$—$(CH_2)_t(C_3$-$C_{10}$ cycloalkyl), and —$C(O)NR^{64}$—$(CH_2)_t(4$-10 membered heterocycloalkyl), wherein t is an integer from 0 to 4, each $R^{64}$ independently represents H or $C_1$-$C_8$ alkyl and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Carboxy' refers to the radical —$C(O)OH$.

'Cycloalkyl' refers to cyclic non-aromatic hydrocarbyl groups having from 3 to 10 carbon atoms. Such cycloalkyl groups include, by way of example, single ring structures such as cyclopropyl, cyclobutyl, cyclopentyl, and cyclooctyl.

'Substituted cycloalkyl' refers to a cycloalkyl group as defined above substituted with one or more of those groups recited in the definition of 'substituted' herein, and particularly refers to a cycloalkyl group having 1 or more substituents, for instance from 1 to 5 substituents, and particularly from 1 to 3 substituents, in particular 1 substituent 'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, e.g. cycloheteroalkenyl, and the like having from 1 to 5, and particularly from 1 to 3 heteroatoms.

'Heteroaryl' means an aromatic ring structure, monocyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

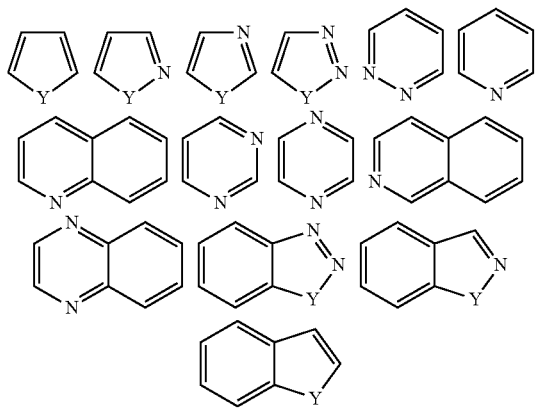

wherein each Y is selected from carbonyl, N, $NR^{65}$, O and S; and $R^{65}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

Examples of representative aryl having hetero atoms containing substitution include the following:

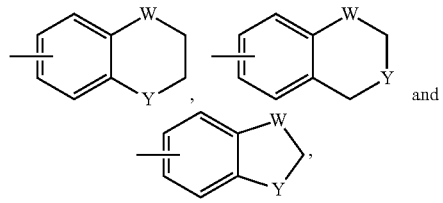

wherein each W is selected from $C(R^{66})_2$, $NR^{66}$, O and S; and each Y is selected from carbonyl, $NR^{66}$, O and S; and $R^{66}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

As used herein, the term 'heterocycloalkyl' refers to a 4-10 membered, stable heterocyclic non-aromatic ring and/or including rings containing one or more heteroatoms independently selected from N, O and S, fused thereto. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

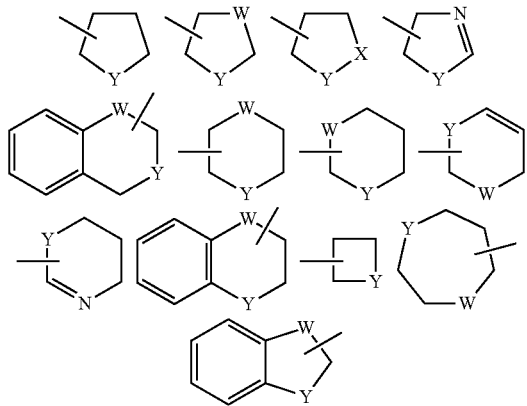

wherein each W is selected from $CR^{67}$, $C(R^{67})_2$, $NR^{67}$, O and S; and each Y is selected from $NR^{67}$, O and S; and $R^{67}$ is independently hydrogen, $C_1$-$C_8$ alkyl, $C_3$-$C_{10}$ cycloalkyl, 4-10 membered heterocycloalkyl, $C_6$-$C_{10}$ aryl, 5-10 membered heteroaryl, These heterocycloalkyl rings may be optionally substituted with one or more groups selected from the group consisting of: acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

'Hydroxy' refers to the radical —OH.
'Nitro' refers to the radical —NO$_2$.
'Substituted' refers to a group in which one or more hydrogen atoms are each independently replaced with the same or different substituent(s). Typical substituents may be selected from the group consisting of:
halogen, —$R^{68}$, —O$^-$, =O, —OR$^{68}$, —SR$^{68}$, —S$^-$, =S, —NR$^{68}$R$^{69}$, =NR$^{68}$, —CCl$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{68}$, —OS(O$_2$)O$^-$, —OS(O)$_2$R$^{68}$, —P(O)(O$^-$)$_2$, —P(O)(OR$^{68}$)(O$^-$), —OP(O)(OR$^{68}$)(OR$^{69}$), —C(O)R$^{68}$, —C(S)R$^{68}$, —C(O)OR$^{68}$, —C(O)NR$^{68}$R$^{69}$, —C(O)O$^-$, —C(S)OR$^{68}$, —NR$^{70}$C(O)NR$^{68}$R$^{69}$, —NR$^{70}$C(S)NR$^{68}$R$^{69}$, —NR$^{71}$C(NR$^{70}$)NR$^{68}$R$^{69}$ and —C(NR$^{70}$)NR$^{68}$R$^{69}$;

wherein each $R^{68}$, $R^{69}$, $R^{70}$ and $R^{71}$ are independently:
hydrogen, $C_1$-$C_8$ alkyl, $C_6$-$C_{10}$ aryl, arylalkyl, $C_3$-$C_{10}$ cycloalkyl, 4-10 membered heterocycloalkyl, 5-10 membered heteroaryl, heteroarylalkyl; or
$C_1$-$C_8$ alkyl substituted with halo or hydroxy; or
$C_6$-$C_{10}$ aryl, 5-10 membered heteroaryl, $C_6$-$C_{10}$ cycloalkyl or 4-10 membered heterocycloalkyl each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

In a particular embodiment, substituted groups are substituted with one or more substituents, particularly with 1 to 3 substituents, in particular with one substituent group.

In a further particular embodiment the substituent group or groups are selected from halo, cyano, nitro, trifluoromethyl, trifluoromethoxy, azido, —NR$^{72}$SO$_2$R$^{73}$, —SO$_2$NR$^{73}$R$^{72}$, —C(O)R$^{73}$, —C(O)OR$^{73}$, —OC(O)R$^{73}$, —NR$^{72}$C(O)R$^{73}$, —C(O)NR$^{73}$R$^{72}$, —NR$^{73}$R$^{72}$, —(CR$^{72}$R$^{72}$)$_m$OR$^{72}$, wherein, each R$^{73}$ is independently selected from H, $C_1$-$C_8$ alkyl, —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), and —(CH$_2$)$_t$(4-10 membered heterocycloalkyl), wherein t is an integer from 0 to 4; and any alkyl groups present, may themselves be substituted by halo or hydroxy; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Each R" independently represents H or $C_1$-$C_6$alkyl.

'Substituted sulfanyl' refers to the group —SR$^{74}$, wherein R$^{74}$ is selected from:
$C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
$C_1$-$C_8$ alkyl substituted with halo, substituted or unsubstituted amino, or hydroxy; or
$C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'substituted sulfanyl' groups are —S—($C_1$-$C_8$ alkyl) and —S—($C_3$-$C_{10}$ cycloalkyl), —S—(CH$_2$)$_t$($C_6$-$C_{10}$ aryl), —S—(CH$_2$)$_t$(5-10 membered heteroaryl), —S—(CH$_2$)$_t$($C_3$-$C_{10}$ cycloalkyl), and —S—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. The term 'substituted sulfanyl' includes the groups 'alkylsulfanyl' or 'alkylthio', 'substituted alkylthio' or 'substituted alkylsulfanyl', 'cycloalkylsulfanyl' or 'cycloalkylthio', 'substituted cycloalkylsulfanyl' or 'substituted cycloalkylthio', 'arylsulfanyl' or 'arylthio' and 'heteroarylsulfanyl' or 'heteroarylthio' as defined below.

'Alkylthio' or 'Alkylsulfanyl' refers to a radical —$SR^{75}$ where $R^{75}$ is a $C_1$-$C_8$ alkyl or group as defined herein. Representative examples include, but are not limited to, methylthio, ethylthio, propylthio and butylthio.

'Substituted Alkylthio' or 'substituted alkylsulfanyl' refers to the group —$SR^{76}$ where $R^{76}$ is a $C_1$-$C_8$ alkyl, substituted with halo, substituted or unsubstituted amino, or hydroxy.

'Cycloalkylthio' or 'Cycloalkylsulfanyl' refers to a radical —$SR^{77}$ where $R^{77}$ is a $C_3$-$C_{10}$ cycloalkyl or group as defined herein. Representative examples include, but are not limited to, cyclopropylthio, cyclohexylthio, and cyclopentylthio.

'Substituted cycloalkylthio' or 'substituted cycloalkylsulfanyl' refers to the group —$SR^{78}$ where $R^{78}$ is a $C_3$-$C_{10}$ cycloalkyl, substituted with halo, substituted or unsubstituted amino, or hydroxy.

'Arylthio' or 'Arylsulfanyl' refers to a radical —$SR^{79}$ where $R^{79}$ is a $C_6$-$C_{10}$ aryl group as defined herein.

'Heteroarylthio' or 'Heteroarylsulfanyl' refers to a radical —$SR^{80}$ where $R^{80}$ is a 5-10 membered heteroaryl group as defined herein.

'Substituted sulfinyl' refers to the group —$S(O)R^{81}$, wherein $R^{81}$ is selected from:
  $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
  $C_1$-$C_8$ alkyl substituted with halo, substituted or unsubstituted amino, or hydroxy; or
  $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'substituted sulfinyl' groups are —$S(O)$—($C_1$-$C_8$ alkyl) and —$S(O)$—($C_3$-$C_{10}$ cycloalkyl), —$S(O)$—$(CH_2)_t(C_6$-$C_{10}$ aryl), —$S(O)$—$(CH_2)_t$(5-10 membered heteroaryl), —$S(O)$—$(CH_2)_t(C_3$-$C_{10}$ cycloalkyl), and —$S(O)$—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. The term substituted sulfinyl includes the groups 'alkylsulfinyl', 'substituted alkylsulfinyl', 'cycloalkylsulfinyl', 'substituted cycloalkylsulfinyl', 'arylsulfinyl' and 'heteroarylsulfinyl' as defined herein.

'Alkylsulfinyl' refers to a radical —$S(O)R^{82}$ where $R^{82}$ is a $C_1$-$C_8$ alkyl group as defined herein. Representative examples include, but are not limited to, methylsulfinyl, ethylsulfinyl, propylsulfinyl and butylsulfinyl.

'Substituted Alkylsulfinyl' refers to a radical —$S(O)R^{83}$ where $R^{83}$ is a $C_1$-$C_8$ alkyl group as defined herein, substituted with halo, substituted or unsubstituted amino, or hydroxy.

'Cycloalkylsulfinyl' refers to a radical —$S(O)R^{84}$ where $R^{84}$ is a $C_3$-$C_{10}$ cycloalkyl or group as defined herein. Representative examples include, but are not limited to, cyclopropylsulfinyl, cyclohexylsulfinyl, and cyclopentylsulfinyl. Exemplary 'cycloalkylsulfinyl' groups are $S(O)$—$C_3$-$C_{10}$ cycloalkyl.

'Substituted cycloalkylsulfinyl' refers to the group —$S(O)R^{85}$ where $R^{85}$ is a $C_3$-$C_{10}$ cycloalkyl, substituted with halo, substituted or unsubstituted amino, or hydroxy.

'Arylsulfinyl' refers to a radical —$S(O)R^{86}$ where $R^{86}$ is a $C_6$-$C_{10}$ aryl group as defined herein.

'Heteroarylsulfinyl' refers to a radical —$S(O)R^{87}$ where $R^{87}$ is a 5-10 membered heteroaryl group as defined herein.

'Substituted sulfonyl' refers to the group —$S(O)_2R^{88}$, wherein $R^{88}$ is selected from:
  $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
  $C_1$-$C_8$ alkyl substituted with halo, substituted or unsubstituted amino, or hydroxy; or
  $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'substituted sulfonyl' groups are —$S(O)_2$—($C_1$-$C_8$ alkyl) and —$S(O)_2$—($C_3$-$C_{10}$ cycloalkyl), —$S(O)_2$—$(CH_2)_t(C_6$-$C_{10}$ aryl), —$S(O)_2$—$(CH_2)_t$(5-10 membered heteroaryl), —$S(O)_2$—$(CH_2)_t(C_3$-$C_{10}$ cycloalkyl), and —$S(O)_2$—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. The term substituted sulfonyl includes the groups alkylsulfonyl, substituted alkylsulfonyl, cycloalkylsulfonyl, substituted cycloalkylsulfonyl, arylsulfonyl and heteroarylsulfonyl.

'Alkylsulfonyl' refers to a radical —$S(O)_2R^{89}$ where $R^{89}$ is an $C_1$-$C_8$ alkyl group as defined herein. Representative examples include, but are not limited to, methylsulfonyl, ethylsulfonyl, propylsulfonyl and butylsulfonyl.

'Substituted Alkylsulfonyl' refers to a radical —$S(O)_2R^{90}$ where $R^{90}$ is an $C_1$-$C_8$ alkyl group as defined herein, substituted with halo, substituted or unsubstituted amino, or hydroxy.

'Cycloalkylsulfonyl' refers to a radical —$S(O)_2R^{91}$ where $R^{91}$ is a $C_3$-$C_{10}$ cycloalkyl or group as defined herein. Representative examples include, but are not limited to, cyclopropylsulfonyl, cyclohexylsulfonyl, and cyclopentylsulfonyl.

'Substituted cycloalkylsulfonyl' refers to the group —$S(O)_2R^{92}$ where $R^{92}$ is a $C_3$-$C_{10}$ cycloalkyl, substituted with halo, substituted or unsubstituted amino, or hydroxy.

'Arylsulfonyl' refers to a radical —$S(O)_2R^{93}$ where $R^{93}$ is an $C_6$-$C_{10}$ aryl group as defined herein.

'Heteroarylsulfonyl' refers to a radical —$S(O)_2R^{94}$ where $R^{94}$ is an 5-10 membered heteroaryl group as defined herein.

'Sulfo' or 'sulfonic acid' refers to a radical such as —$SO_3H$.

'Substituted sulfo' or 'sulfonic acid ester' refers to the group —$S(O)_2OR^{95}$, wherein $R^{95}$ is selected from:
  $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
  $C_1$-$C_8$ alkyl substituted with halo, substituted or unsubstituted amino, or hydroxy; or
  $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'Substituted sulfo' or 'sulfonic acid ester' groups are —S(O)$_2$—O—($C_1$-$C_8$ alkyl) and —S(O)$_2$—O—($C_3$-$C_{10}$ cycloalkyl), —S(O)$_2$—O—(CH$_2$)$_t$($C_6$-$C_{10}$ aryl), —S(O)$_2$—O—(CH$_2$)$_t$(5-10 membered heteroaryl), —S(O)$_2$—O—(CH$_2$)$_t$($C_3$-$C_{10}$ cycloalkyl), and —S(O)$_2$—O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Thiol' refers to the group —SH.

'Aminocarbonylamino' refers to the group —NR$^{96}$C(O)NR$^{96}$R$^{96}$ where each R$^{96}$ is independently hydrogen $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl, as defined herein; or where two R$^{96}$ groups, when attached to the same N, are joined to form an alkylene group.

'Bicycloaryl' refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

'Bicycloheteroaryl' refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

'Compounds of the present invention', and equivalent expressions, are meant to embrace the compounds as hereinbefore described, in particular compounds according to any of the formulae herein recited and/or described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

'Cycloalkylalkyl' refers to a radical in which a cycloalkyl group is substituted for a hydrogen atom of an alkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

'Heterocycloalkylalkyl' refers to a radical in which a heterocycloalkyl group is substituted for a hydrogen atom of an alkyl group. Typical heterocycloalkylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

'Cycloalkenyl' refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

'Substituted cycloalkenyl' refers to those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Fused Cycloalkenyl' refers to a cycloalkenyl having two of its ring carbon atoms in common with a second aliphatic or aromatic ring and having its olefinic unsaturation located to impart aromaticity to the cycloalkenyl ring.

'Ethenyl' refers to substituted or unsubstituted —(C=C)—.

'Ethylene' refers to substituted or unsubstituted —(C—C)—.

'Ethynyl' refers to —(C≡C)—.

'Hydrogen bond donor' group refers to a group containing O—H, or N—H functionality. Examples of 'hydrogen bond donor' groups include —OH, —NH$_2$, and —NH—R$^{97}$ and wherein R$^{97}$ is alkyl, acyl, cycloalkyl, aryl, or heteroaryl.

'Dihydroxyphosphoryl' refers to the radical —PO(OH)$_2$.

'Substituted dihydroxyphosphoryl' refers to those groups recited in the definition of "substituted" herein, and particularly refers to a dihydroxyphosphoryl radical wherein one or both of the hydroxyl groups are substituted. Suitable substituents are described in detail below.

'Aminohydroxyphosphoryl' refers to the radical —PO(OH)NH$_2$.

'Substituted aminohydroxyphosphoryl' refers to those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

'Nitrogen-Containing Heterocycloalkyl' group means a 4 to 7 membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

'Thioketo' refers to the group =S.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

'Compounds of the present invention', and equivalent expressions, are meant to embrace compounds of the Formula(e) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

When ranges are referred to herein, for example but without limitation, $C_1$-$C_8$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy) alkyl esters or ((alkoxycarbonyl)oxy)alkylesters. Particularly the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 80% by weight R-compound and at most about 20% by weight S-compound, at least about 90% by weight R-compound and at most about 10% by weight S-compound, at least about 95% by weight R-compound and at most about 5% by weight S-compound, at least about 99% by weight R-compound and at most about 1% by weight S-compound, at least about 99.9% by weight R-compound or at most about 0.1% by weight S-compound. In certain embodiments, the weights are based upon total weight of compound.

As used herein and unless otherwise indicated, the term "enantiomerically pure S-compound" or "S-compound" refers to at least about 80% by weight S-compound and at most about 20% by weight R-compound, at least about 90% by weight S-compound and at most about 10% by weight R-compound, at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds and Processes to Make them

In certain aspects, the present invention provides certain novel compounds useful as intermediates for the preparation of Sitagliptin. In additional aspect, the present invention includes the use of such intermediates in the preparation of Sitagliptin. In yet additional aspect, the invention provides a novel process for the preparation of Sitagliptin.

In certain aspects, the present invention provides certain intermediates useful for preparation of Sitagliptin and pharmaceutically acceptable salt thereof.

In particular aspects, the present invention provides processes for the preparation of an intermediate compound of formula I:

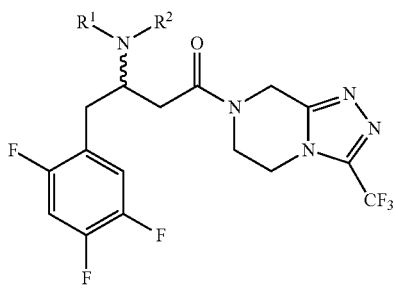

I or a salt thereof; wherein each $R^1$ and $R^2$ is independently H, substituted or unsubstituted alkyl, substituted or unsubstituted alkoxy, substituted or unsubstituted aryl, substituted or unsubstituted aryloxy, substituted or unsubstituted aralkyl, substituted or unsubstituted heterocycloalkyl, or substituted or unsubstituted cycloalkyl, —C(O)—$R^3$, —C(O)—O$R^3$, —O—C(O)—$R^3$, —S(O)$_2$—$R^3$, —Si($R^3$)$_3$, and —O—Si($R^3$)$_3$; each $R^3$ is independently selected from substituted or unsubstituted alkyl, substituted or unsubstituted benzyl, substituted or unsubstituted cycloalkyl, substituted or unsubstituted aryl, and substituted or unsubstituted heteroaryl;

or $R^1$ and $R^2$ are joined together to form a heterocycle; and the wavy bond represents that the compound is in R-, S- or racemic form;

wherein the process comprises the steps of:

A1) providing an intermediate compound of formula II:

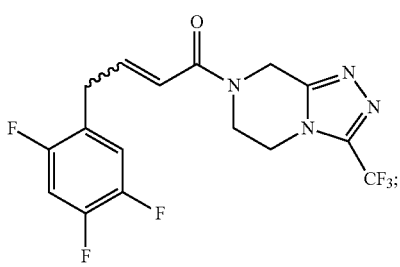

II

A2) reacting the intermediate compound of formula II with a Michael donor of formula III:

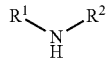

III wherein $R^1$ and $R^2$ are as described above;

to obtain the intermediate compound of formula I.

In one embodiment, each $R^1$ and $R^2$ is H.

In another embodiment, each of $R^1$ and $R^2$ is H, Me, benzyl, —C(O)—O-benzyl, —C(O)—O-t-Bu, —Si(Me)$_3$-CH(Me)-Ph, or —CH(Me)-naphthyl.

In another embodiment, $R^1$ is H; and $R^2$ is t-butyl, substituted or unsubstituted benzyl, —CH(Me)-Ph, or substituted or unsubstituted phenyl.

In another embodiment, $R^1$ is H; and $R^2$ is —CH(Me)-Ph.

In another embodiment, $R^1$ is H; and $R^2$ is —CH(Me)-naphthyl.

In another embodiment, $R^1$ is H; and $R^2$ is —CH(Me)-naphth-2-yl.

In another embodiment, $R^1$ is H; and $R^2$ is 4-methoxyphenyl.

In another embodiment, $R^1$ is H; and $R^2$ is methoxy, benzyloxy, phenoxy, or silyloxy.

In another embodiment, $R^1$ is H; and $R^2$ is tosyloxy [—S(O)$_2$-(4-methylphenyl)].

In another embodiment, $R^1$ is H; and $R^2$ is —C(O)—O-benzyl, or —C(O)—O-t-Bu.

In one embodiment, the Michael donor is selected from ammonia, dimethylamine, t-butylcarbamate, O-methylhydroxylamine, benzylamine, p-methoxybenzylamine, 3,4-dimethoxybenzylamine, p-methoxyaniline, tosylamine, benzylcarbamate, dibenzylamine, naphthylamine, O-benzylhydroxylamine, O-phenylhydroxylamine, benzhydrylamine, methylphenyl-amine, N-z-methylbenzylamine, N-benzyl-1-phenethylamine, hexamethyldisilazane, potassium bis(trimethylsilyl)amide, sodium bis(trimethylsilyl)amide, lithium bis(trimethylsilyl)amide, 1,1,3,3-tetramethyldisilazane, 1,1,3,3-tetramethyl-1,3-diphenylsilazane, O-trimethylsilyl)hydroxylamine, (S)-1-(naphth-2-yl)ethylamine, (R)-1-(naphth-2-yl)ethylamine, and N,O-bis(trimethylsilyl)hydroxylamine.

In one embodiment, the Michael reagent is present in an amount of 1.01 to 3.0 equivalents, 1.1 to 2.0 equivalents, or 1.2 to 1.7 equivalents, with respect to the compound of formula XI.

In one embodiment, the step A2) occurs in the absence of solvent.

In another embodiment, the step A2) occurs in the presence of solvent.

In another embodiment, the step A2) occurs in a solvent selected from the group consisting of methanol, ethanol, isopropyl alcohol, acetonitrile, ethyl acetate, acetone, methyl ethyl ketone, diethyl ether, tetrahydrofuran, N-methyl pyrrolidinone, dimethyl formamide, dimethyl sulfoxide, and combinations thereof.

In another embodiment, the step A2) occurs in a protic solvent.

In another embodiment, the step A2) occurs in a protic solvent selected from the group consisting of methanol, ethanol, isopropyl alcohol, t-butanol, trifluoroethanol, hexafluoro-2-propanol, amyl alcohol, and combinations thereof.

In a particular embodiment, the step A2) occurs in water.

In one embodiment, the step A2) occurs under Michael reaction or Michael addition conditions.

In one embodiment, the step A2) occurs for 1 to 100 hours, 5 to 50 hours, or 6 to 48 hours.

In one embodiment, the step A2) occurs at 50° C. to 100° C., 60° C. to 90° C., 60° C. to 80° C., 60° C. to 70° C., or about 60° C.

In a particular embodiment, the step A2) occurs at about 20° C. to 80° C.

In one embodiment, the step A2) occurs in the absence of a catalyst.

In another embodiment, the step A2) occurs in the presence of a catalyst.

In another embodiment, the step A2) occurs in the presence of a catalyst; and the catalyst is a transition metal catalyst.

In another embodiment, the step A2) occurs in the presence of a catalyst; and the catalyst is selected from copper compounds, indium compounds, iron compounds, manganese compounds, cerium compounds, bismuth compounds, scandium compounds, ytterbium compounds, yttrium compounds, tin compounds, and vanadium compounds. In a particular embodiment, the catalyst is selected from copper (I)acetate, copper(II)triflate, copper(II)bromide, indium(III) chloride, scandium(III)triflate, iron(III)chloride, and vanadium(III)acetylacetonate.

In another embodiment, the catalyst is present in an amount of 2-25 mol %, 4-20 mol % or 8-15 mol % with respect to the compound of formula II.

In another embodiment, the step A2) occurs in the presence of a catalyst; and the catalyst is a transition metal catalyst; and in the presence of a base.

In another embodiment, the step A2) occurs in the presence of a catalyst; and the catalyst is a transition metal catalyst; and in the absence of a base.

In another embodiment, the step A2) occurs in the presence of a catalyst; and the catalyst is a transition metal catalyst; and in the presence of a base; and the base is selected from sodium t-butoxide, potassium t-butoxide, potassium carbonate, sodium carbonate, potassium acetate, sodium acetate, and any combination thereof.

In another embodiment, the step A2) occurs in the presence of an acid.

In another embodiment, the step A2) occurs in the presence of an acid; and the acid is a Lewis acid or Bronsted acid.

In another embodiment, the step A2) occurs in the presence of a chiral organocatalyst.

In one embodiment, the step A2) occurs in the presence of a promoter.

In another embodiment, the step A2) occurs in the presence of a promoter; and the promoter is a fluorinated alcohol or combination thereof.

In another embodiment, the step A2) occurs in the presence of a surfactant.

In another embodiment, the process is used in a preparation of sitagliptin or a salt of sitagliptin.

In another aspect, the present invention provides stereoselective processes for the preparation of a pharmaceutically acceptable salt of sitagliptin of formula IV:

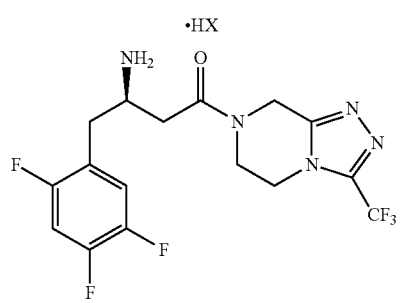

IV or a solvate, or polymorph thereof; wherein HX is a pharmaceutically acceptable acid;

comprising the steps of:

B1) reacting the compound of formula II or an isomer thereof:

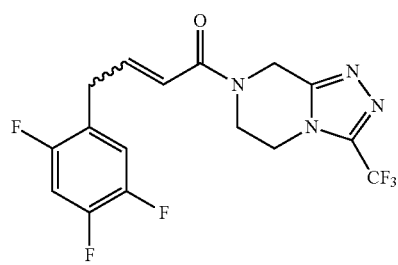

II with a Michael donor of formula III:

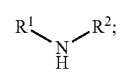

III wherein each $R^1$ and $R^2$ is H; or $R^1$ is H, and $R^2$ is t-butyl, 1,1,1-triphenylmethyl, or —C(O)—O-t-Bu;

to form a mixture of isomers according to formula Va and Vb:

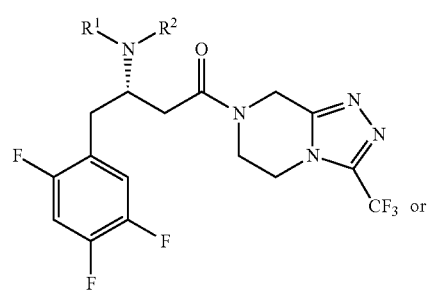

Va or

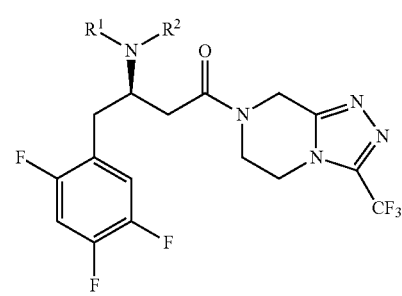

Vb

B2) separating the compound of formula Vb from the mixture of isomers;

B3) reacting the compound of formula Vb with HX to produce the pharmaceutically acceptable salt of sitagliptin of formula IV or a solvate, or polymorph thereof.

In yet another aspect, the present invention provides stereoselective process for the preparation of a pharmaceutically acceptable salt of sitagliptin of formula IV:

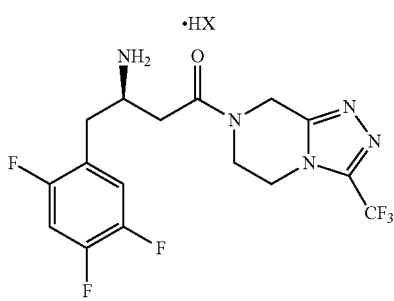

or a solvate, or polymorph thereof; wherein HX is a pharmaceutically acceptable acid; comprising the steps of:

C1) reacting the compound of formula II or an isomer thereof:

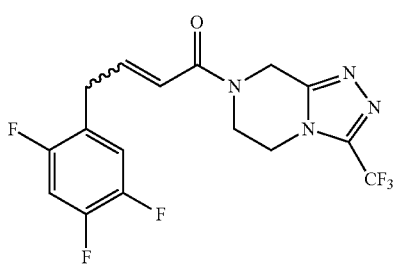

with a Michael donor of formula III:

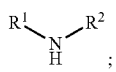

wherein $R^1$ is H, and $R^2$ is substituted or unsubstituted benzyl, —C(O)—O-benzyl, —CH(Me)-Ph, —CH(Me)-naphth-2-yl, or —CH(Ph)-C(O)OR$^{4a}$, —CH(Ph)-C(O)NR$^{4a}$R$^{4b}$; each R$^{4a}$ and R$^{4b}$ is independently H, substituted or unsubstituted alkyl, benzyl, or substituted or unsubstituted cycloalkyl; or $R^1$ and $R^2$ are joined together to form a heterocycle; and Ph is substituted or unsubstituted phenyl;

to form a mixture of isomers according to formula Va and Vb:

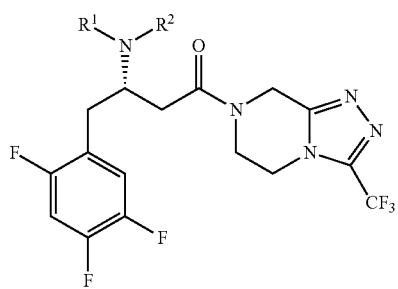

or

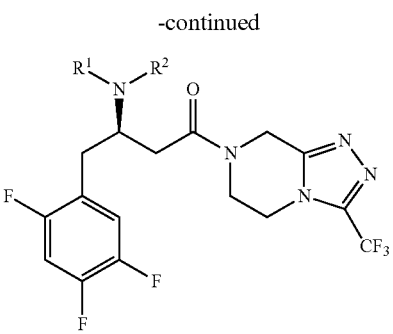

C2) separating the compound of formula Vb from the mixture of isomers;

C3) reacting the compound of formula Vb with HX to obtain the salt of formula VI:

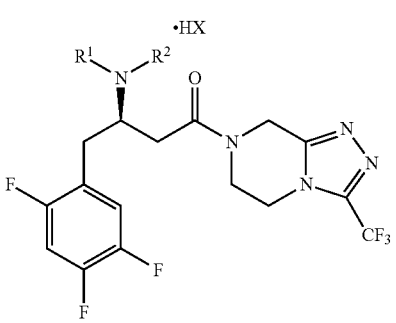

C4) hydrogenolysis of the compound of formula VI or a solvate or polymorph, thereof; to produce the pharmaceutically acceptable salt of sitagliptin of formula IV or a solvate, or polymorph thereof.

In one embodiment, $R^1$ is H; and $R^2$ is benzyl or —C(O)—O-benzyl.

In one embodiment, $R^{4a}$ is H, Me, Et, n-Pr, i-Pr, n-Bu, cyclopropyl, cyclobutyl, cyclopentyl, cyclohexyl, or cycloheptyl.

In one embodiment, $R^{4b}$ is H, Me, Et, n-Pr, i-Pr, n-Bu, cyclopropyl, cyclobutyl, cyclopentyl, cyclohexyl, or cycloheptyl.

In another embodiment, each $R^{4a}$ and $R^{4b}$ is H; and Ph is unsubstituted phenyl.

In one embodiment, the Michael donor is

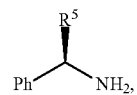

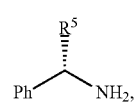

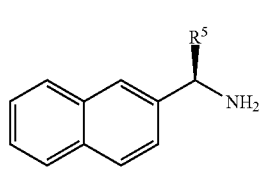

or

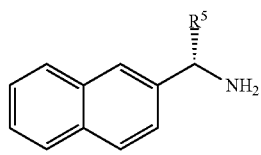

VIId

Ph is substituted or unsubstituted phenyl, $R^5$ is substituted or unsubstituted alkyl, —$CONR^{4a}R^{4b}$, or —$COOR^{4a}$; and $R^{4a}$, $R^{4b}$ and Ph are as described herein.

In one embodiment, the Michael donor is (S)-1-(naphth-2-yl)ethylamine, or (R)-1-(naphth-2-yl)ethylamine.

In another embodiment, the Michael donor is VIIa; and the step A2) or C1) produces a mixture of isomers according to formula VIIIa and VIIIb:

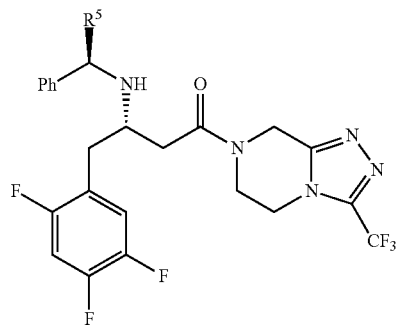

VIIIa

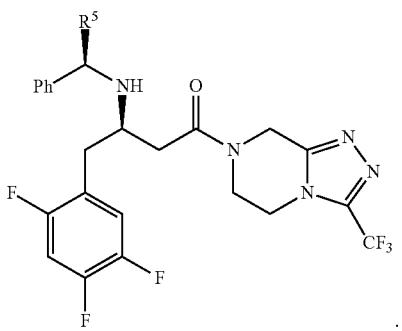

VIIIb

In another embodiment, the Michael donor is VIIb; and the step A2) or C1) produces a mixture of isomers according to formula IXa and IXb:

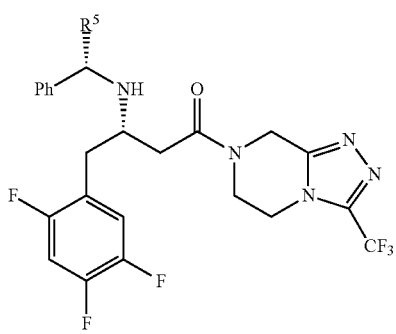

IXa

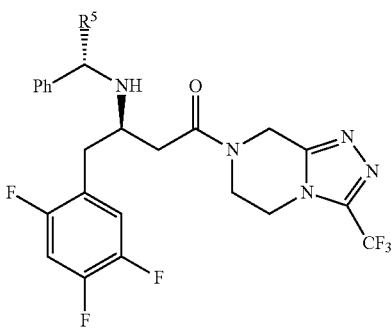

IXb

In another embodiment, the Michael donor is VIIa; and the step C3) produces a compound according to formula Xa:

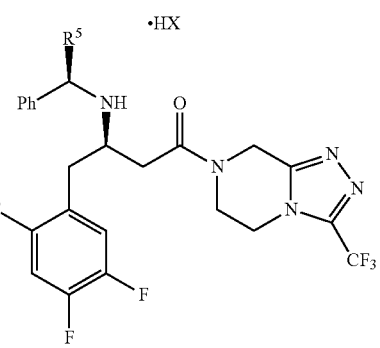

Xa

In another embodiment, the Michael donor is VIIb; and the step C3) produces a compound according to formula Xb:

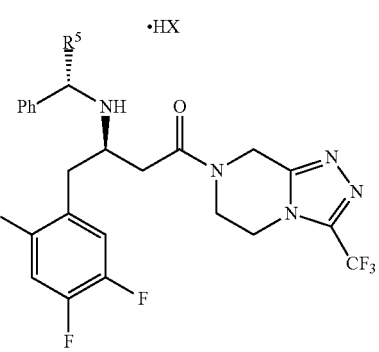

Xb

In one embodiment, $R^5$ is substituted or unsubstituted alkyl.

In another embodiment, $R^5$ is unsubstituted alkyl, or hydroxyalkyl.

In another embodiment, $R^5$ is Me, Et, n-Pr, i-Pr, n-Bu, hydroxymethyl, or hydroxyethyl.

In another embodiment, $R^5$ is —COOH.

In another embodiment, $R^5$ is —COOMe or —COOEt.

In another embodiment, $R^5$ is —$CONH_2$.

In one embodiment, the step B1) or C0 occurs in the absence of solvent.

In another embodiment, the step B1) or C1) occurs in the presence of solvent.

In another embodiment, the step B1) or C1) occurs in a solvent selected from the group consisting of methanol, ethanol, isopropyl alcohol, acetonitrile, ethyl acetate, acetone, methyl ethyl ketone, diethyl ether, tetrahydrofuran, N-methyl pyrrolidinone, dimethyl formamide, dimethyl sulfoxide, and combinations thereof.

In another embodiment, the step B1) or C1) occurs in a protic solvent.

In another embodiment, the step B1) or C1) occurs in a protic solvent selected from the group consisting of methanol, ethanol, isopropyl alcohol, t-butanol, trifluoroethanol, hexafluoro-2-propanol, amyl alcohol, and combinations thereof.

In another embodiment, the step B1) or C1) occurs in water.

In another embodiment, the step B1) or C1) occurs under Michael reaction or Michael addition conditions.

In another embodiment, the step B1) or C1) occurs for 1 to 100 hours, 5 to 50 hours, or 6 to 48 hours.

In another embodiment, the step B1) or C1) occurs at 50° C. to 100° C., 60° C. to 90° C., 60° C. to 80° C., 60° C. to 70° C., or about 60° C.

In another embodiment, the step B1) or C1) occurs at about 20° C. to 80° C.

In another embodiment, the step B1) or C1) occurs in the absence of a catalyst.

In another embodiment, the step B1) or C1) occurs in the presence of a catalyst.

In another embodiment, the step B1) or C1) occurs in the presence of a catalyst; and the catalyst is a transition metal catalyst.

In another embodiment, the step B1) or C1) occurs in the presence of a catalyst; and the catalyst is selected from copper compounds, indium compounds, iron compounds, manganese compounds, cerium compounds, bismuth compounds, scandium compounds, ytterbium compounds, yttrium compounds, tin compounds, and vanadium compounds. In a particular embodiment, the catalyst is selected from copper(I)acetate, copper(II)triflate, copper(II)bromide, indium(III)chloride, scandium(III)triflate, iron(III)chloride, and vanadium(III)acetylacetonate.

In another embodiment, the catalyst is present in an amount of 2-25 mol %, 4-20 mol % or 8-15 mol % with respect to the compound of formula II.

In another embodiment, the step B1) or C1) occurs in the presence of a catalyst; and the catalyst is a transition metal catalyst; and in the presence of a base.

In another embodiment, the step B1) or C1) occurs in the presence of a catalyst; and the catalyst is a transition metal catalyst; and in the absence of a base.

In another embodiment, the step B1) or C1) occurs in the presence of a catalyst; and the catalyst is a transition metal catalyst; and in the presence of a base; and the base is selected from sodium t-butoxide, potassium t-butoxide, potassium carbonate, sodium carbonate, potassium acetate, sodium acetate, and any combination thereof.

In another embodiment, the step B1) or C1) occurs in the presence of an acid.

In another embodiment, the step B1) or C1) occurs in the presence of an acid; and the acid is a Lewis acid or Bronsted acid.

In another embodiment, the step B1) or C1) occurs in the presence of a chiral organocatalyst.

In another embodiment, the step B1) or C1) occurs in the presence of a promoter.

In another embodiment, the step B1) or C1) occurs in the presence of a promoter; and the promoter is a fluorinated alcohol or combination thereof.

In another embodiment, the step B1) or C1) occurs in the presence of a surfactant.

In another embodiment, the step B2) or C2) occurs by crystallization.

In another embodiment, the step B2) or C2) occurs by crystallization, and the crystallization occurs in a solvent selected from the group consisting of methanol, ethanol, isopropyl alcohol, acetonitrile, or ethyl acetate.

In another embodiment, the step B3) or C3) occurs in a solvent selected from the group consisting of methanol, ethanol, isopropyl alcohol, acetonitrile, ethyl acetate, acetone, methyl ethyl ketone, diethyl ether, tetrahydrofuran, N-methyl pyrrolidinone, dimethyl formamide, dimethyl sulfoxide, and combinations thereof.

In another embodiment, the step B3) or C3) occurs in isopropanol.

In another embodiment, the step B3) or C3) occurs in the presence of HX.

In another embodiment, the step B3) or C3) occurs in the presence of HX; and HX is phosphoric, acetic, oxalic, methane sulfonic, benzenesulfonic, benzoic, citric, fumaric, hydrochloric, hydrobromic, lactic, malic or maleic acid.

In another embodiment, the step B3) or C3) occurs in the presence of HX; and HX is phosphoric acid.

In another embodiment, the step B3) or C3) occurs in the presence of $H_3PO_4$.

In another embodiment, the step B3) or C3) occurs at a temperature from about 0° C. to about 100° C.

In another embodiment, the step B3) or C3) occurs at a temperature around 70° C.

In another embodiment, the step B4) or C4) occurs in a solvent selected from the group consisting of water, methanol, ethanol, isopropyl alcohol, acetonitrile, ethyl acetate, acetone, methyl ethyl ketone, diethyl ether, tetrahydrofuran, N-methyl pyrrolidinone, dimethyl formamide, dimethyl sulfoxide, and combinations thereof.

In another embodiment, the step B4) or C4) occurs in a combination of isopropanol and water.

In another embodiment, the step B4) or C4) occurs under catalytic hydrogenolysis conditions.

In another embodiment, the step B4) or C4) occurs in the presence of hydrogen gas.

In another embodiment, the step B4) or C4) occurs in the presence of Pd/C.

In a particular aspect, the present invention provides compounds according to formula XI:

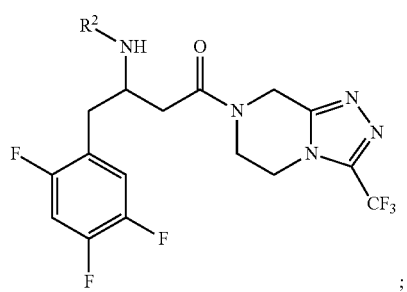

XI or a solvate, polymorph, pharmaceutically acceptable salt or isomer thereof;

wherein R² is —CO—NR⁴ᵃR⁴ᵇ, —C(H)(R⁵)-Ph, or —C(H)(R⁵)-naphthyl;

each R⁴ᵃ and R⁴ᵇ is independently H, substituted or unsubstituted alkyl, benzyl, or substituted or unsubstituted cycloalkyl; or R⁴ᵃ and R⁴ᵇ are joined together to form a heterocycle;

R⁵ is substituted methyl, substituted or unsubstituted C₂-C₆ alkyl, or —COOR⁴ᵃ;

Ph is substituted or unsubstituted phenyl;

provided that when each of R⁴ᵃ and R⁴ᵇ is H; then the compound is in a form of an acid addition salt.

In another particular aspect, the present invention provides compounds according to formula XII:

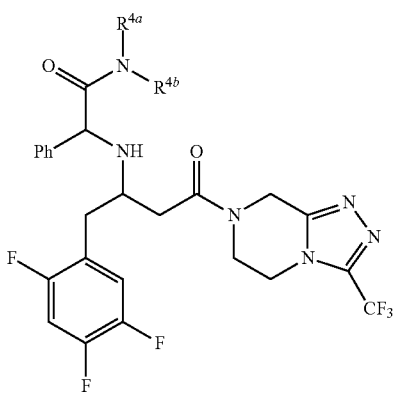

XII or a solvate, polymorph, pharmaceutically acceptable salt or isomer thereof;

wherein each R⁴ᵃ and R⁴ᵇ is independently H, substituted or unsubstituted alkyl, benzyl, or substituted or unsubstituted cycloalkyl; or R⁴ᵃ and R⁴ᵇ are joined together to form a heterocycle; Ph is substituted or unsubstituted phenyl;

provided that when each of R⁴ᵃ and R⁴ᵇ is H; then the compound is in a form of an acid addition salt.

In one embodiment, with respect to the compound of formula XI, the compound is according to formula XIIa or XIIb:

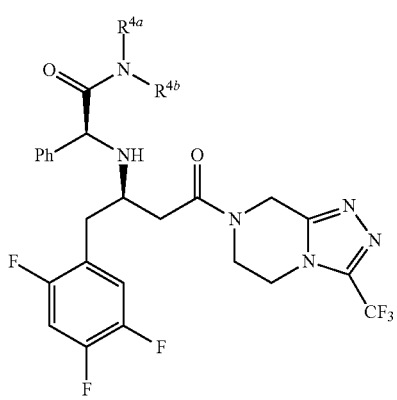

XIIa

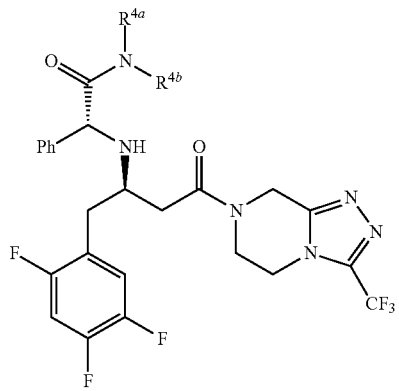

XIIb or a solvate, polymorph, pharmaceutically acceptable salt thereof; and each R⁴ᵃ and R⁴ᵇ is as described for formula XI.

In one embodiment, with respect to the compound of formula XI, the compound is an acid addition salt; and the acid is phosphoric, acetic, methane sulfonic, benzenesulfonic, benzoic, citric, fumaric, hydrochloric, hydrobromic, lactic, malic or maleic acid.

In one embodiment, with respect to the compound of formula XI, each of R⁴ᵃ and R⁴ᵇ is H; the compound is an acid addition salt; and the acid is phosphoric, acetic, methane sulfonic, benzenesulfonic, benzoic, citric, fumaric, hydrochloric, hydrobromic, lactic, malic or maleic acid.

In one embodiment, with respect to the compound of formula XI, R⁴ᵃ is H, Me, Et, n-Pr, i-Pr, n-Bu, cyclopropyl, cyclobutyl, cyclopentyl, cyclohexyl, or cycloheptyl.

In one embodiment, with respect to the compound of formula XI, R⁴ᵇ is H, Me, Et, n-Pr, i-Pr, n-Bu, cyclopropyl, cyclobutyl, cyclopentyl, cyclohexyl, or cycloheptyl.

In one embodiment, with respect to the compound of formula XI, the compound is according to formula XIIIa or XIIIb:

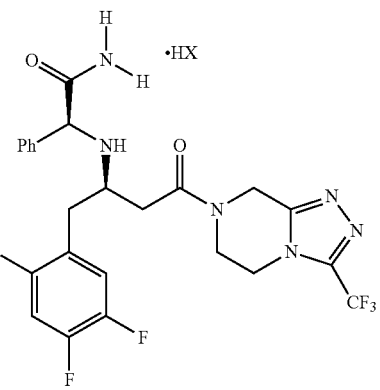

XIIIa or

XIIIb

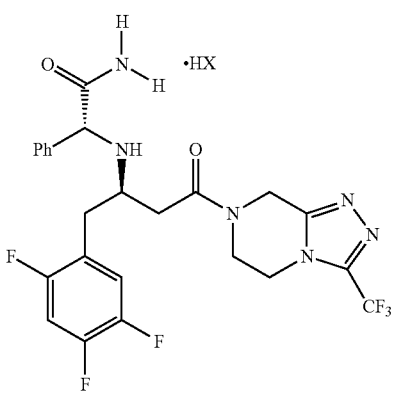 [SMILES: CNC(=O)C(NC(CC(=O)N1CCn2c(nnc2C(F)(F)F)C1)Cc1cc(F)c(F)cc1F)c1ccccc1]

or a solvate, or polymorph thereof.

In one embodiment, HX is a pharmaceutically acceptable acid; and the acid is phosphoric, acetic, methane sulfonic, benzenesulfonic, benzoic, citric, fumaric, hydrochloric, hydrobromic, lactic, malic or maleic acid.

In one embodiment, HX is a pharmaceutically acceptable acid; and the acid is phosphoric acid.

In one embodiment, Ph is unsubstituted phenyl.

In one embodiment, with respect to the compound of formula XI, the compound is according to formula XVIa, XVIb, XVIc, or XVId:

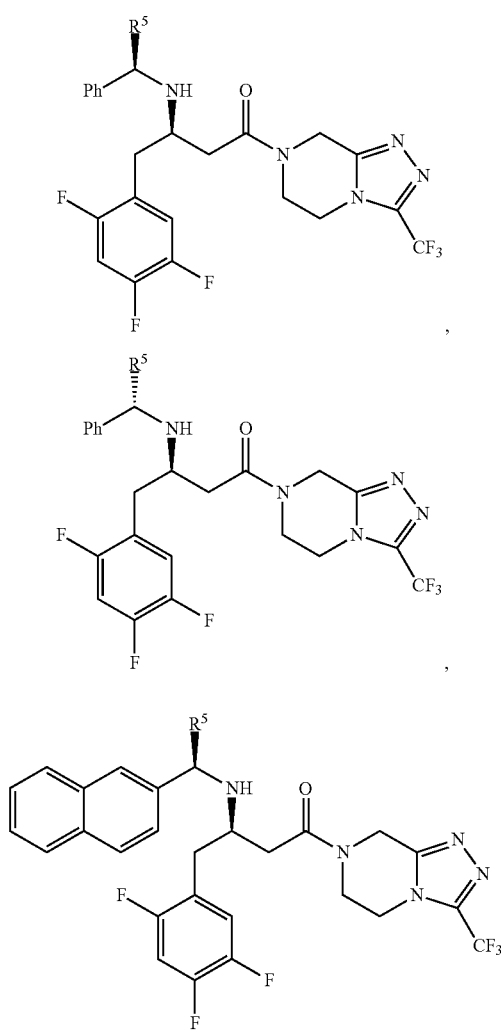

XVId

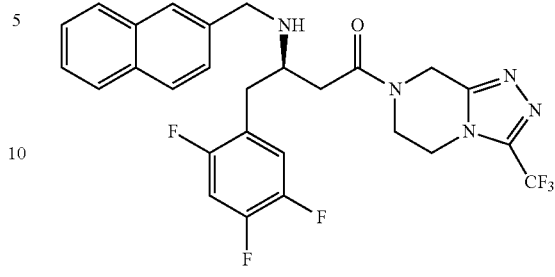

or a solvate, polymorph, or isomer thereof; and Ph is substituted or unsubstituted phenyl, $R^5$ is substituted methyl, substituted or unsubstituted $C_2$-$C_6$ alkyl, or —$COOR^{4a}$; and $R^{4a}$ is as described herein; or Ph is substituted phenyl, and $R^5$ is Me.

In one embodiment, with respect to the compound of formula XI, the compound is according to formula XVa, or XVb:

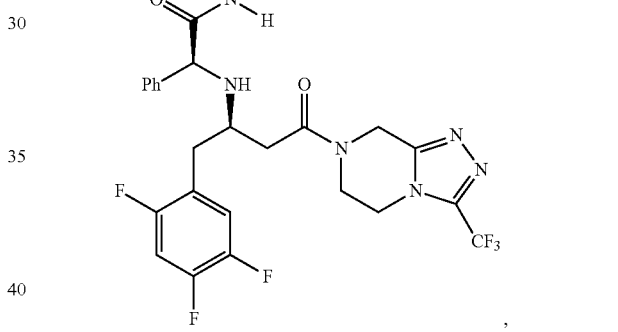

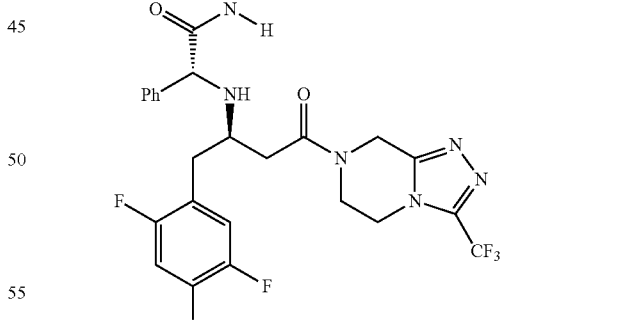

or a solvate, or polymorph thereof; and Ph is unsubstituted phenyl.

In one embodiment, with respect to the compound of formula XI, the compound is a solvate.

In one embodiment, with respect to the compound of formula XI, the compound is a hydrate.

In another particular aspect, the present invention provides compounds according to formula XVIa, XVIb, XVIc, or XVId:

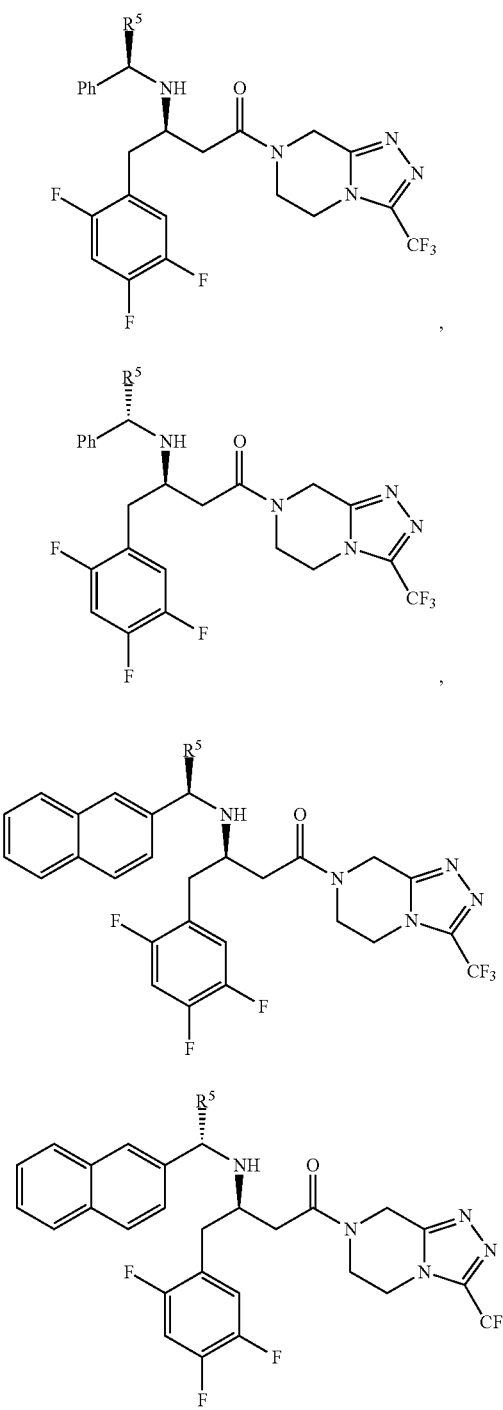

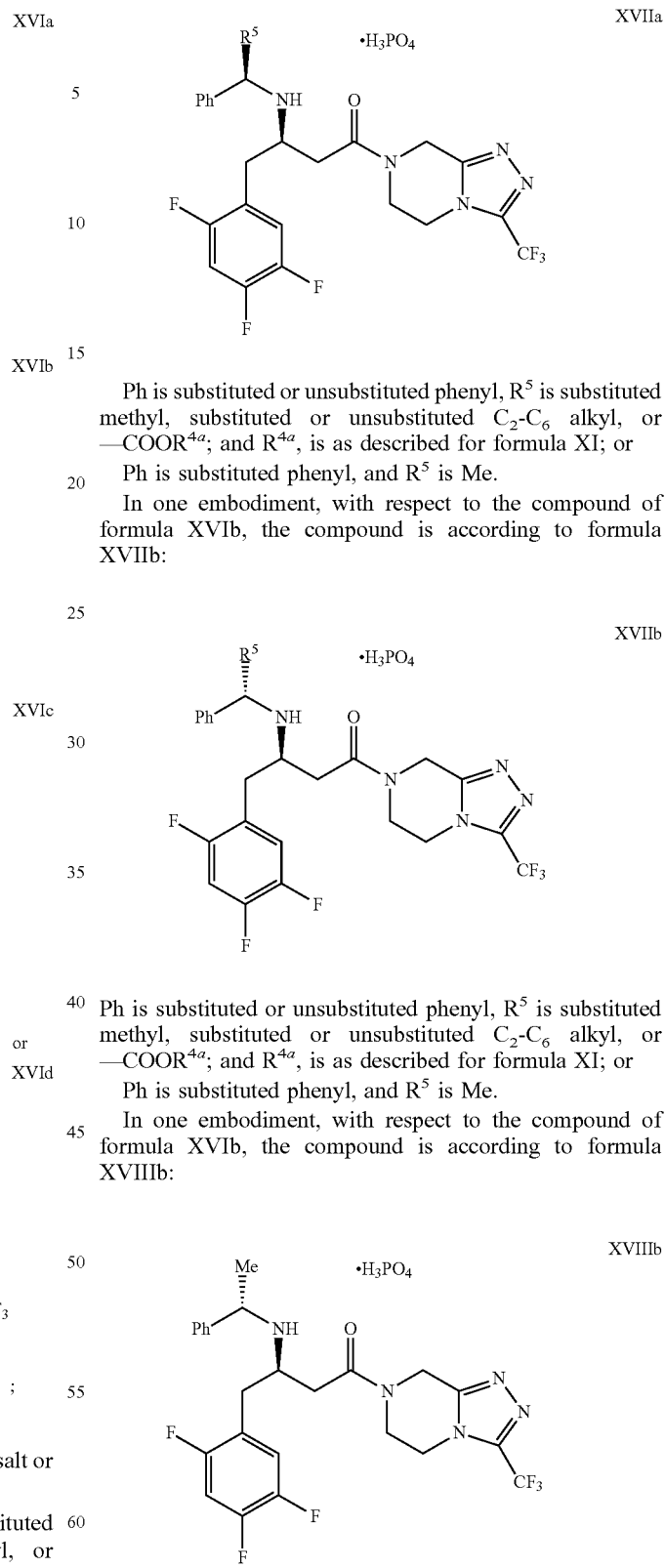

or a solvate, polymorph, pharmaceutically acceptable salt or isomer thereof;

Ph is substituted or unsubstituted phenyl, $R^5$ is substituted methyl, substituted or unsubstituted $C_2$-$C_6$ alkyl, or —COOR$^{4a}$; and $R^{4a}$, is as described for formula XI; or Ph is substituted phenyl, and $R^5$ is Me.

In one embodiment, with respect to the compound of formula XVIb, the compound is according to formula XVIIa:

Ph is substituted or unsubstituted phenyl, $R^5$ is substituted methyl, substituted or unsubstituted $C_2$-$C_6$ alkyl, or —COOR$^{4a}$; and $R^{4a}$, is as described for formula XI; or Ph is substituted phenyl, and $R^5$ is Me.

In one embodiment, with respect to the compound of formula XVIb, the compound is according to formula XVIIb:

Ph is substituted or unsubstituted phenyl, $R^5$ is substituted methyl, substituted or unsubstituted $C_2$-$C_6$ alkyl, or —COOR$^{4a}$; and $R^{4a}$, is as described for formula XI; or Ph is substituted phenyl, and $R^5$ is Me.

In one embodiment, with respect to the compound of formula XVIb, the compound is according to formula XVIIIb:

Ph is substituted or unsubstituted phenyl.

In one embodiment, with respect to the compound of formula XI, the compound is according to formula XIXa or XIXb:

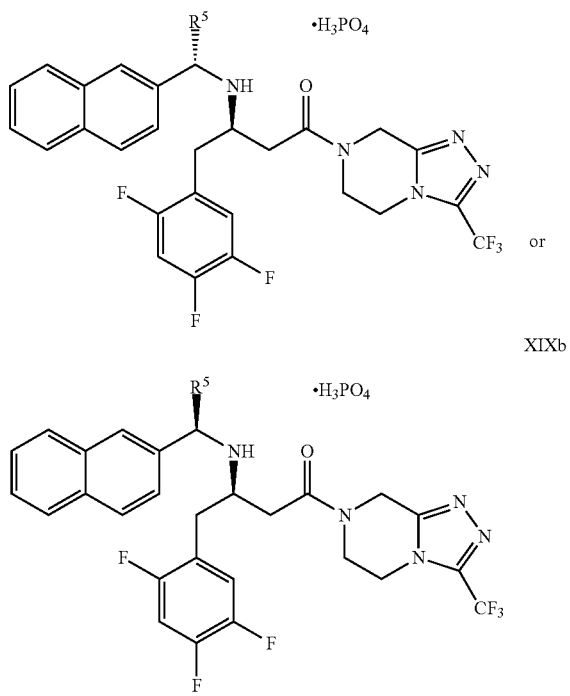

XIXa

XIXb $R^5$ is substituted or unsubstituted $C_1$-$C_6$ alkyl, or —COOR$^{4a}$; and R$^{4a}$, is as in claim 91.

In one particular embodiment, R$^5$ is Me.

In one embodiment, with respect to the compound of formula XI, the compound is according to formula XXa or XXb:

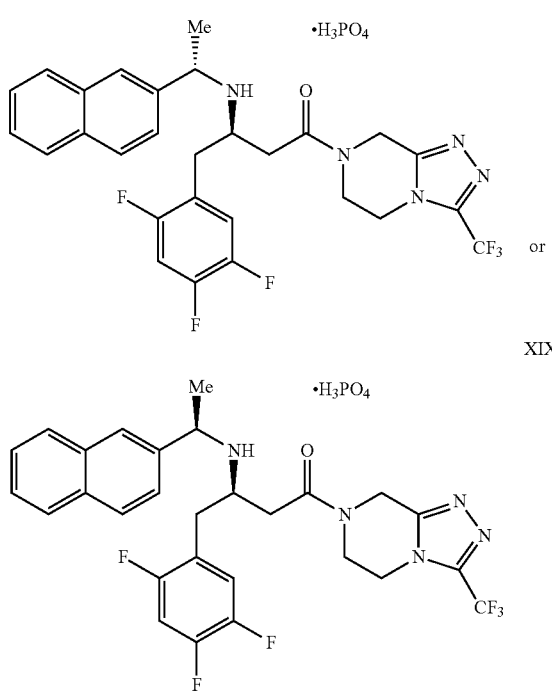

XIXa

XIXb

In a further aspect, the invention provides composition of compounds listed in Table 1.

In a further aspect, the invention provides the use of any one of compounds according to formulae V, Vb, VI, VIIIa, VIIIb, Xb, XI, XIIa, XIIb, XIIIa, XIIIb, XIV, XVa, XVb, XVIa, XVIb, XVIIa, XVIIb, XVIIIb, XIXa, or XIXb in the preparation of Sitagliptin.

In a further aspect, the invention provides the use of any one of compounds selected from the compounds listed in Table 1 in the preparation of Sitagliptin.

In one embodiment, the invention provides a compound selected from the compounds listed in Table 1.

In one embodiment, the invention provides the use of any one of compounds according to formulae V, Vb, VI, VIIIa, VIIIb, Xb, XI, XIIa, XIIb, XIIIa, XIIIb, XIV, XVa, XVb, XVIa, XVIb, XVIIa, XVIIb, XVIIIb, XIXa, or XIXb in the preparation of Sitagliptin.

In one embodiment, the invention provides the use of any one of compounds selected from V, Vb, VI, VIIIa, VIIIb, Xb, XI, XIIa, XIIb, XIIIa, XIIIb, XIV, XVa, XVb, XVIa, XVIb, XVIIa, XVIIb, XVIIIb, XIXa, or XIXb in the preparation of Sitagliptin.

In one particular embodiment, HX is acetic acid. In another particular embodiment, HX is oxalic acid. In another particular embodiment, HX is benzenesulfonic acid.

In another particular embodiment, HX is phosphoric acid.

In one embodiment, the invention provides the use of any one of compounds selected from the compounds listed in Table 1 in the preparation of Sitagliptin.

In yet another particular aspect, the present invention provides stereoselective process for the preparation of a pharmaceutically acceptable salt of sitagliptin of formula IV″:

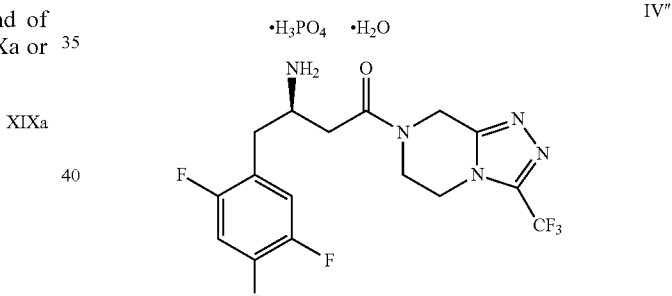

IV″ or polymorph thereof; comprising the steps of:
D1) reacting the compound of formula II or an isomer thereof:

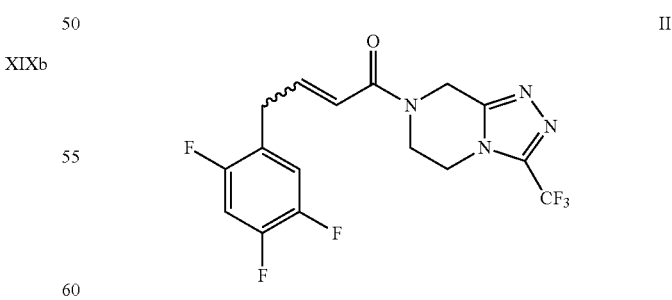

II with a Michael donor of formula XXI:

XXI to form a mixture of isomers according to formula XXIIa and XXIIb:

XXIIa

[Chemical structure: (S)-configured compound with Me/Ph group on NH, linked via CH2-C(=O) to triazolopyrazine with CF3, and 2,4,5-trifluorobenzyl group]

XXIIb

[Chemical structure: (R)-configured isomer of the above compound]

D2) separating the compound of formula XXIIb from the mixture of isomers;
D3) reacting the compound of formula XXIIb with phosphoric acid to obtain the salt of formula XVIIIb:

XVIIIb

[Chemical structure: compound XXIIb · H₃PO₄ salt]

D4) hydrogenolysis of the compound of formula XVIIIb or a solvate or polymorph, thereof; to produce the monohydrate of the phosphate salt of sitagliptin according to the formula IV''', or polymorph thereof.

In one embodiment, the phosphoric acid in the step D3) is replaced with oxalic acid to form the oxalate salt (XVIIIb: H₃PO₄ is replaced with oxalic acid).

In one embodiment, the phosphoric acid in the step D3) is replaced with benzenesulfonic acid to form the benzene sulfonate salt (XVIIIb: H₃PO₄ is replaced with benzenesulfonic acid).

In one embodiment, Ph is unsubstituted phenyl.
In one embodiment, the step D1) occurs in the absence of solvent.

In another embodiment, the step D1) occurs in the presence of solvent.

In another embodiment, the step D1) occurs in a solvent selected from the group consisting of methanol, ethanol, isopropyl alcohol, acetonitrile, ethyl acetate, acetone, methyl ethyl ketone, diethyl ether, tetrahydrofuran, N-methyl pyrrolidinone, dimethyl formamide, dimethyl sulfoxide, and combinations thereof.

In another embodiment, the step D1) occurs in a protic solvent.

In another embodiment, the step D1) occurs in a protic solvent selected from the group consisting of methanol, ethanol, isopropyl alcohol, t-butanol, trifluoroethanol, hexafluoro-2-propanol, amyl alcohol, and combinations thereof.

In another embodiment, the step D1) occurs in water.
In another embodiment, the step D1) occurs under Michael reaction or Michael addition conditions.

In another embodiment, the step D1) occurs for 1 to 100 hours, 5 to 50 hours, or 6 to 48 hours.

In another embodiment, the step D1) occurs at 50° C. to 100° C., 60° C. to 90° C., 60° C. to 80° C., 60° C. to 70° C., or about 60° C.

In another embodiment, the step D1) occurs at about 20° C. to 80° C.

In another embodiment, the step D1) occurs in the absence of a catalyst.

In another embodiment, the step D1) occurs in the presence of a catalyst.

In another embodiment, the step D1) occurs in the presence of a catalyst; and the catalyst is a transition metal catalyst.

In another embodiment, the step D1) occurs in the presence of a catalyst; and the catalyst is selected from copper compounds, indium compounds, iron compounds, manganese compounds, cerium compounds, bismuth compounds, scandium compounds, ytterbium compounds, yttrium compounds, tin compounds, and vanadium compounds. In a particular embodiment, the catalyst is selected from copper (I)acetate, copper(II)triflate, copper(II)bromide, indium(III) chloride, scandium(III)triflate, iron(III)chloride, and vanadium(III)acetylacetonate.

In another embodiment, the catalyst is present in an amount of 2-25 mol %, 4-20 mol % or 8-15 mol % with respect to the compound of formula II.

In another embodiment, the step D1) occurs in the presence of a catalyst; and the catalyst is a transition metal catalyst; and in the presence of a base.

In another embodiment, the step D1) occurs in the presence of a catalyst; and the catalyst is a transition metal catalyst; and in the absence of a base.

In another embodiment, the step D1) occurs in the presence of a catalyst; and the catalyst is a transition metal catalyst; and in the presence of a base; and the base is selected from sodium t-butoxide, potassium t-butoxide, potassium carbonate, sodium carbonate, potassium acetate, sodium acetate, and any combination thereof.

In another embodiment, the step D1) occurs in the presence of an acid.

In another embodiment, the step D1) occurs in the presence of an acid; and the acid is a Lewis acid or Bronsted acid.

In another embodiment, the step D1) occurs in the presence of a chiral organocatalyst.

In another embodiment, the step D1) occurs in the presence of a promoter.

In another embodiment, the step D1) occurs in the presence of a promoter; and the promoter is a fluorinated alcohol or combination thereof.

In another embodiment, the step D1) occurs in the presence of a surfactant.

In another embodiment, the step D2) occurs by crystallization.

In another embodiment, the step D2) occurs by precipitation.

In another embodiment, the step D2) occurs by crystallization, and the crystallization occurs in a solvent selected from the group consisting of methanol, ethanol, isopropyl alcohol, acetonitrile, or ethyl acetate.

In another embodiment, the step D3) occurs in a solvent selected from the group consisting of methanol, ethanol, isopropyl alcohol, acetonitrile, ethyl acetate, acetone, methyl ethyl ketone, diethyl ether, tetrahydrofuran, N-methyl pyrrolidinone, dimethyl formamide, dimethyl sulfoxide, and combinations thereof.

In another embodiment, the step D3) occurs in isopropanol.

In another embodiment, the step D3) occurs at a temperature from about 0° C. to about 100° C.

In another embodiment, the step D3) occurs at a temperature around 70° C.

In another embodiment, the step D4) occurs in a solvent selected from the group consisting of water, methanol, ethanol, isopropyl alcohol, acetonitrile, ethyl acetate, acetone, methyl ethyl ketone, diethyl ether, tetrahydrofuran, N-methyl pyrrolidinone, dimethyl formamide, dimethyl sulfoxide, and combinations thereof.

In another embodiment, the step D4) occurs in a combination of isopropanol and water.

In another embodiment, the step D4) occurs under catalytic hydrogenolysis conditions.

In another embodiment, the step D4) occurs in the presence of hydrogen gas.

In another embodiment, the step D4) occurs in the presence of Pd/C.

Additional embodiments within the scope of the present invention are set forth in non-limiting fashion elsewhere herein and in the examples. It should be understood that these examples are for illustrative purposes only and are not to be construed as limiting this invention in any manner.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholinyl esters and the like.

Certain compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ or $C_1$-$C_6$alkyl, $C_2$-$C_8$ alkenyl, aryl, substituted aryl, and arylalkyl esters of the compounds of the invention.

GENERAL SYNTHETIC PROCEDURES

The compounds of this invention can be prepared from readily available starting materials using the following general methods and procedures. See, e.g., Synthetic Scheme, below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, N.Y., 1991, and references cited therein.

The compounds of this invention, for example, may be prepared by the reaction of a chloro derivative with an appropriately substituted amine and the product isolated and purified by known standard procedures. Such procedures include (but are not limited to) recrystallization, column chromatography or HPLC. The following schemes are presented with details as to the preparation of representative fused heterocyclics that have been listed hereinabove. The compounds of the invention may be prepared from known or commercially available starting materials and reagents by one skilled in the art of organic synthesis.

The compounds of the present invention may be prepared by a variety of processes well known for the preparation of compounds of this type, for example reaction schemes. and general procedures as described herein.

The syntheses of representative compounds of this invention are carried out in accordance with the methods set forth above and using the appropriate reagents, starting materials, and purification methods known to those skilled in the art. All starting materials in the following general syntheses may be commercially available or obtained by conventional methods known to those skilled in the art.

As used herein, the following abbreviations have the following definitions:

BEP 2-bromo-1-ethylpyridinium tetrafluoroborate

BOP benzotriazol-1-yloxy-tris(dimethylamino)phosphonium hexafluorophosphate

CDI 2-chloro-1,3-dimethylimidazolinium chloride

DCC dicyclohexylcarbodiimide

DCM dichloromethane

DME 1,2-dimethoxyethane, dimethoxyethane

DMF N,N-dimethylformamide

DMSO dimethyl sulfoxide

EDC 1-ethyl-3-(3'-dimethylaminopropyl)carbodiimide hydrogen chloride

EtOAc ethyl acetate

EtOH ethanol

HOBt 1-hydroxybenzotriazole

MeOH methanol

NMP N-methyl-2-pyrroliidone

THF tetrahydrofuran

TFA trifluoroacetic acid uM μM uL μL

PREPARATION OF THE COMPOUNDS OF THE INVENTION
Representative Synthetic Schemes
Scheme 1
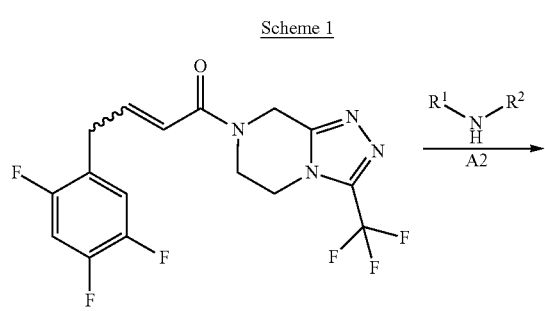
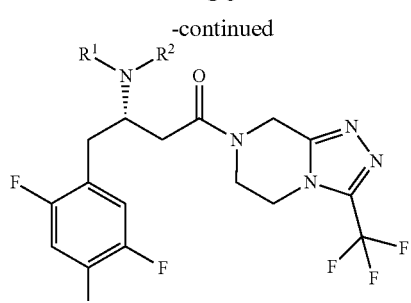
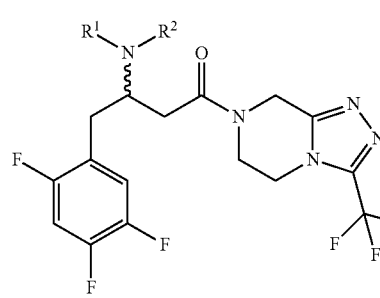
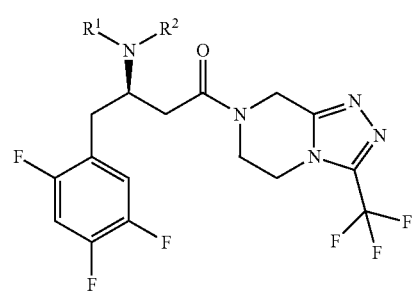
wherein $R^1$ and $R^2$ are as described herein.
Scheme 2
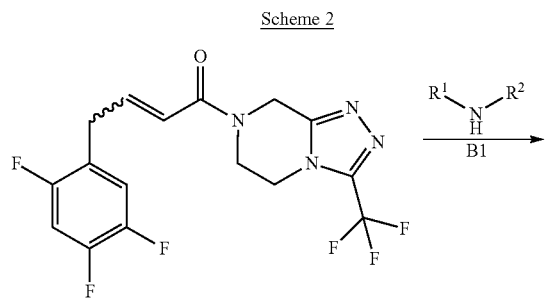
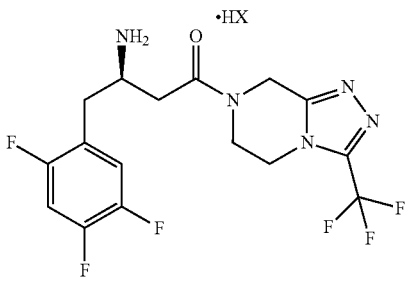
wherein $R^1$ and $R^2$ are as described herein.
Scheme 3
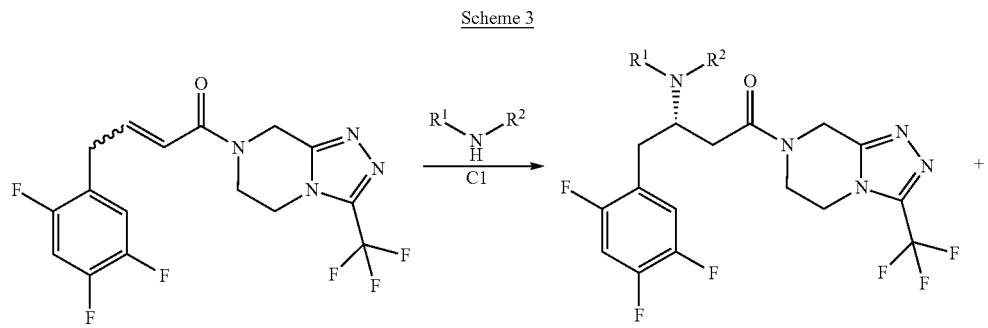

-continued
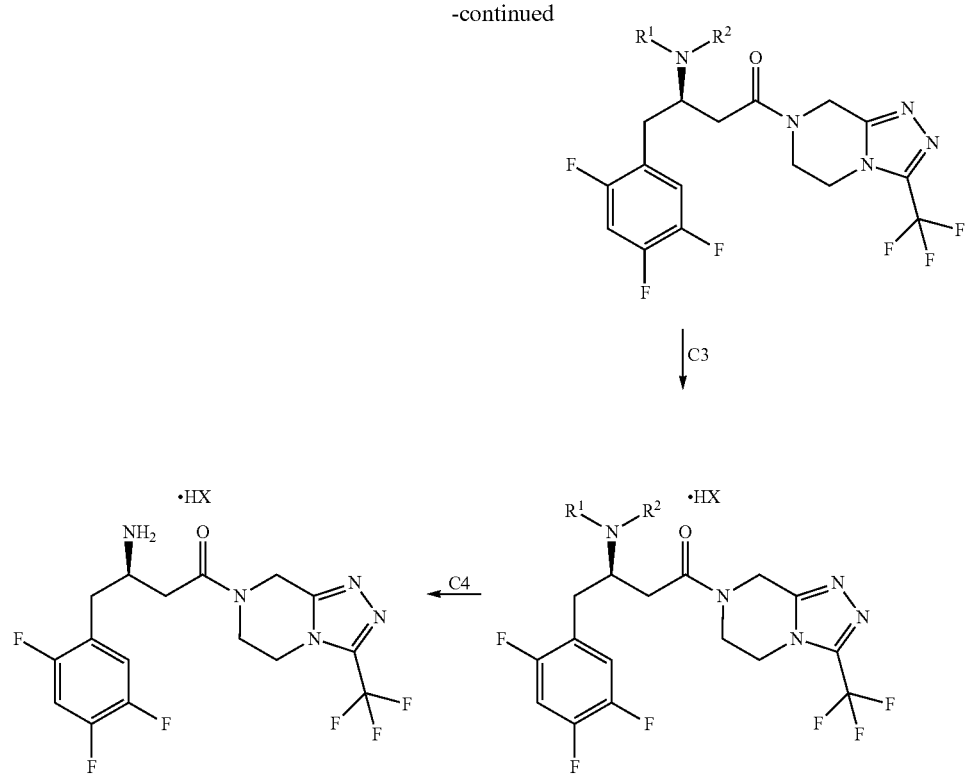
wherein R¹ and R² are as described herein.
Scheme 4
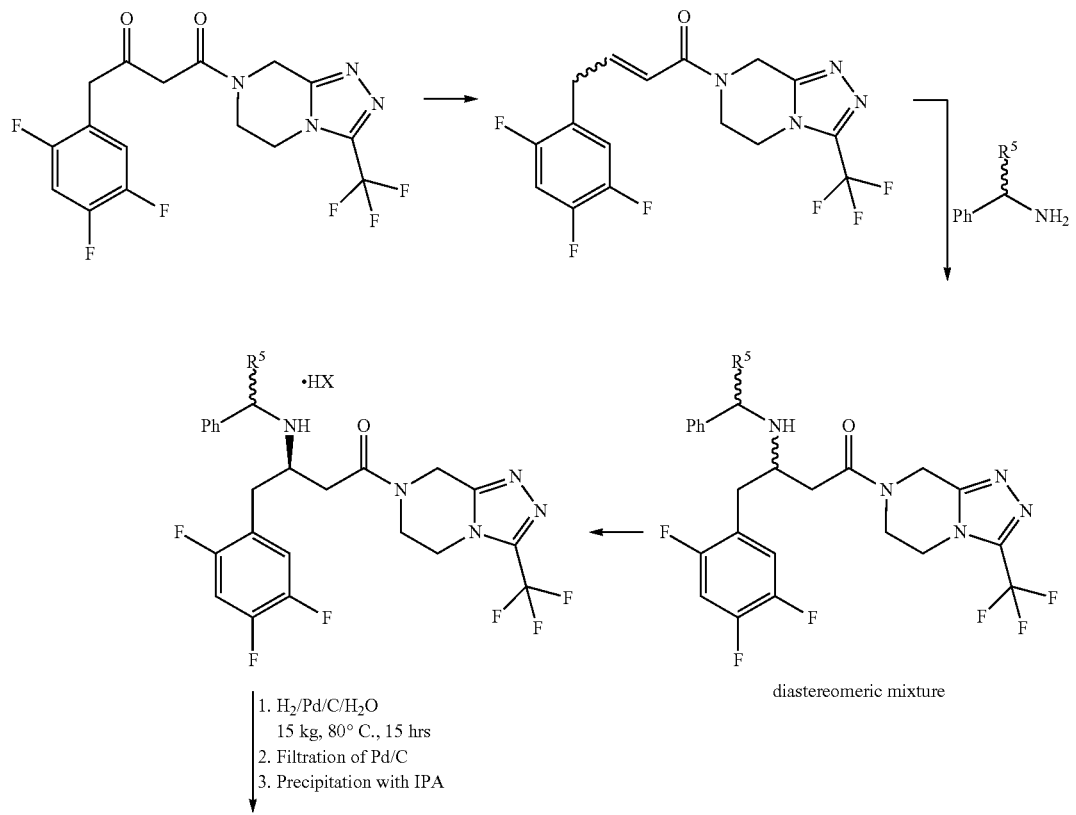
diastereomeric mixture
1. H₂/Pd/C/H₂O
   15 kg, 80° C., 15 hrs
2. Filtration of Pd/C
3. Precipitation with IPA

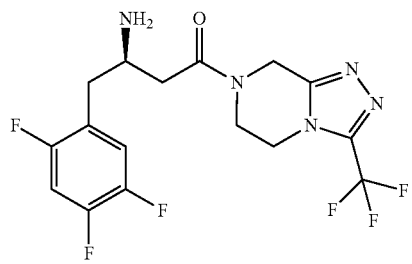
Sitagliptin salt with HX
wherein HX, and R⁵ are as described herein.
Scheme 5
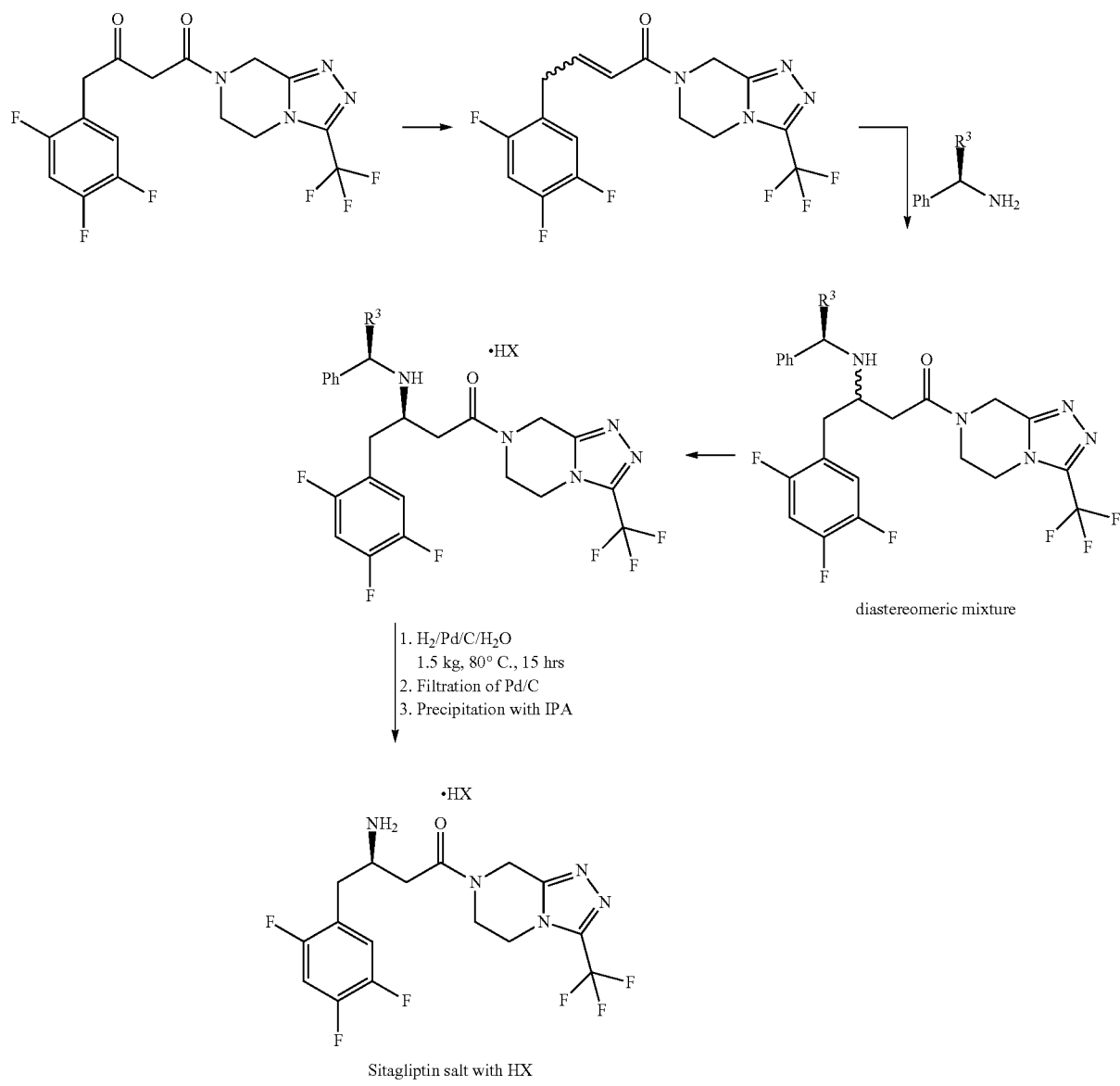
diastereomeric mixture
1. H₂/Pd/C/H₂O
   1.5 kg, 80° C., 15 hrs
2. Filtration of Pd/C
3. Precipitation with IPA
Sitagliptin salt with HX
wherein HX, and R⁵ are as described herein.

Scheme 6
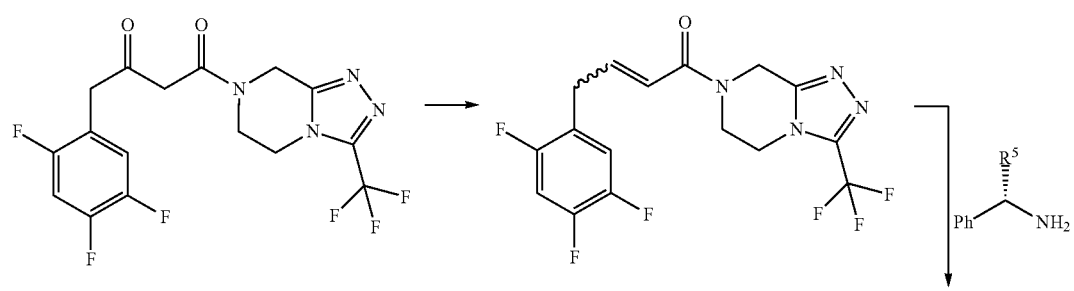
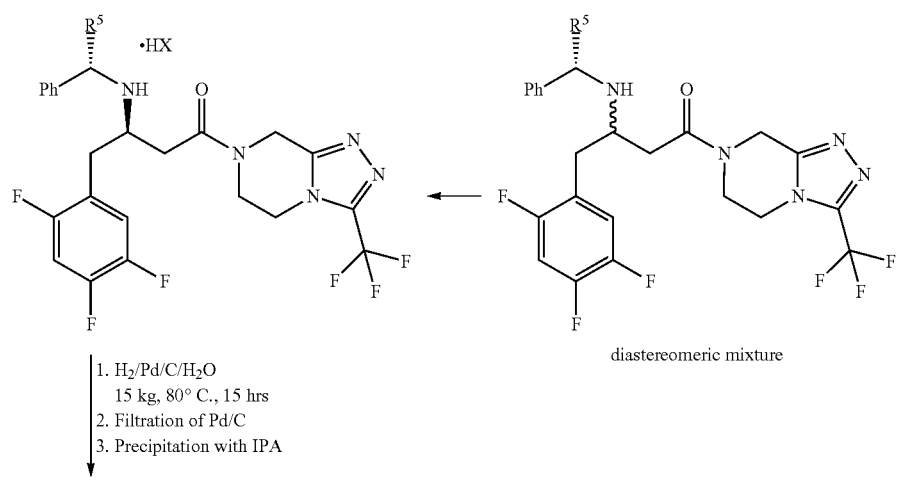
1. H₂/Pd/C/H₂O
   15 kg, 80° C., 15 hrs
2. Filtration of Pd/C
3. Precipitation with IPA
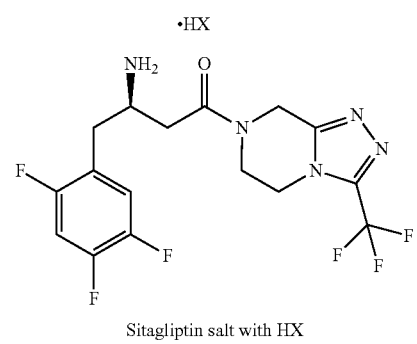
Sitagliptin salt with HX
wherein HX, and R⁵ are as described herein.
Scheme 7
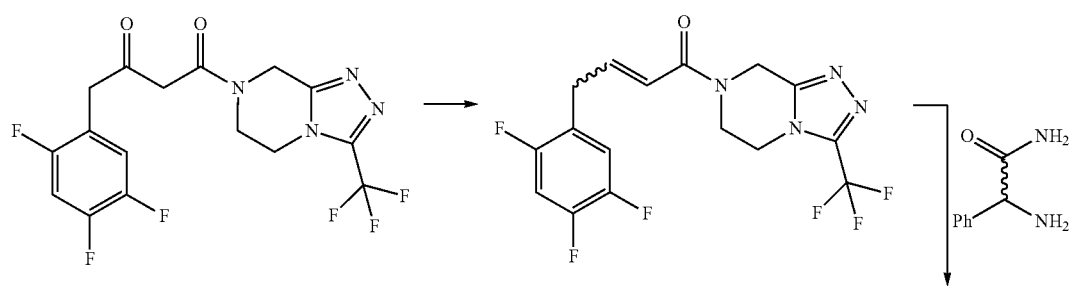

-continued
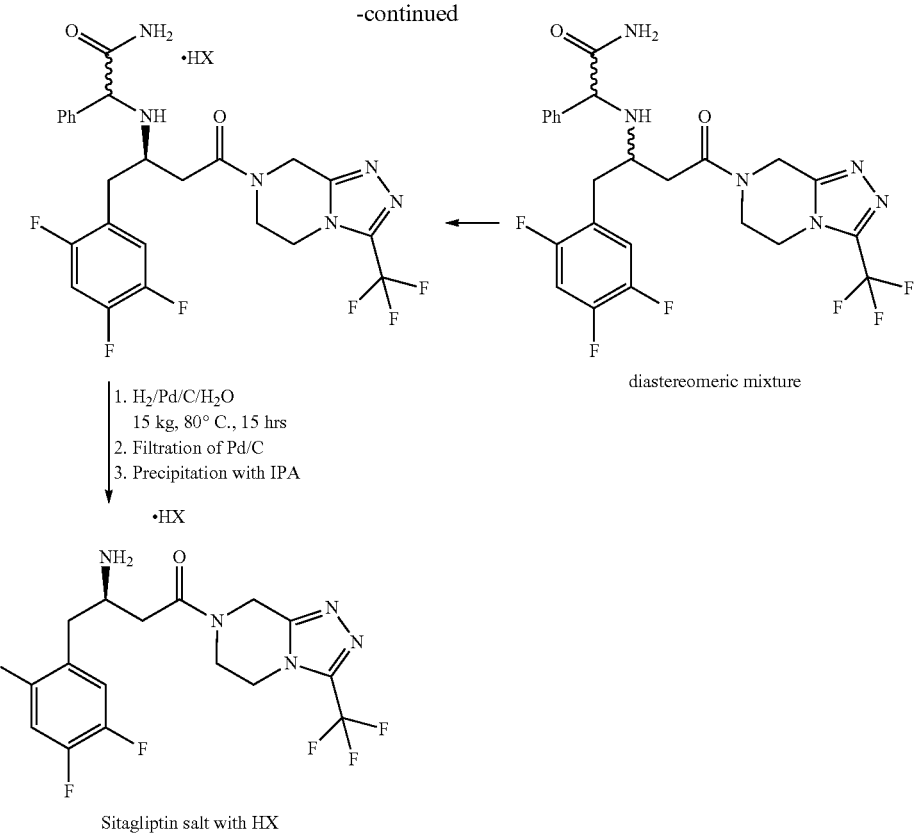
wherein HX are as described herein.
Scheme 8
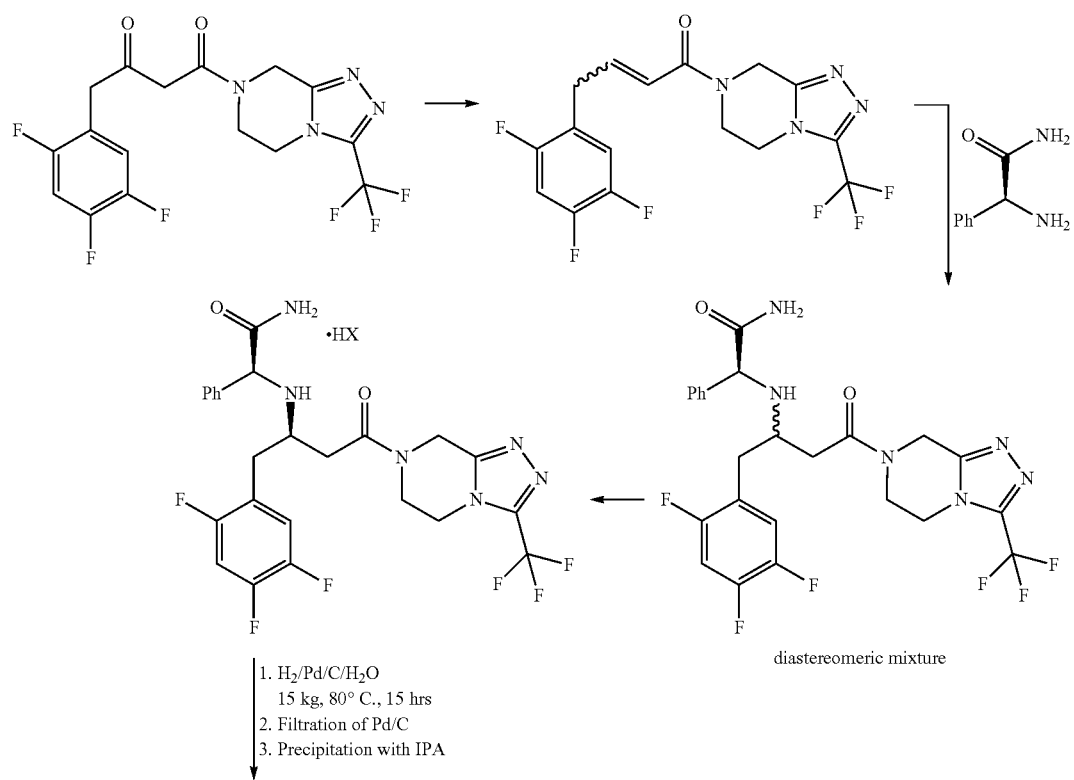

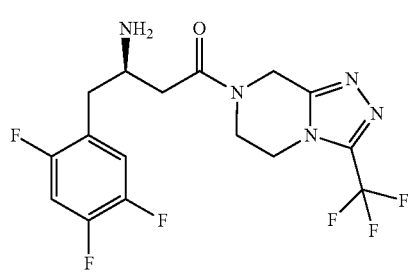
Sitagliptin salt with HX
wherein HX are as described herein.
Scheme 9
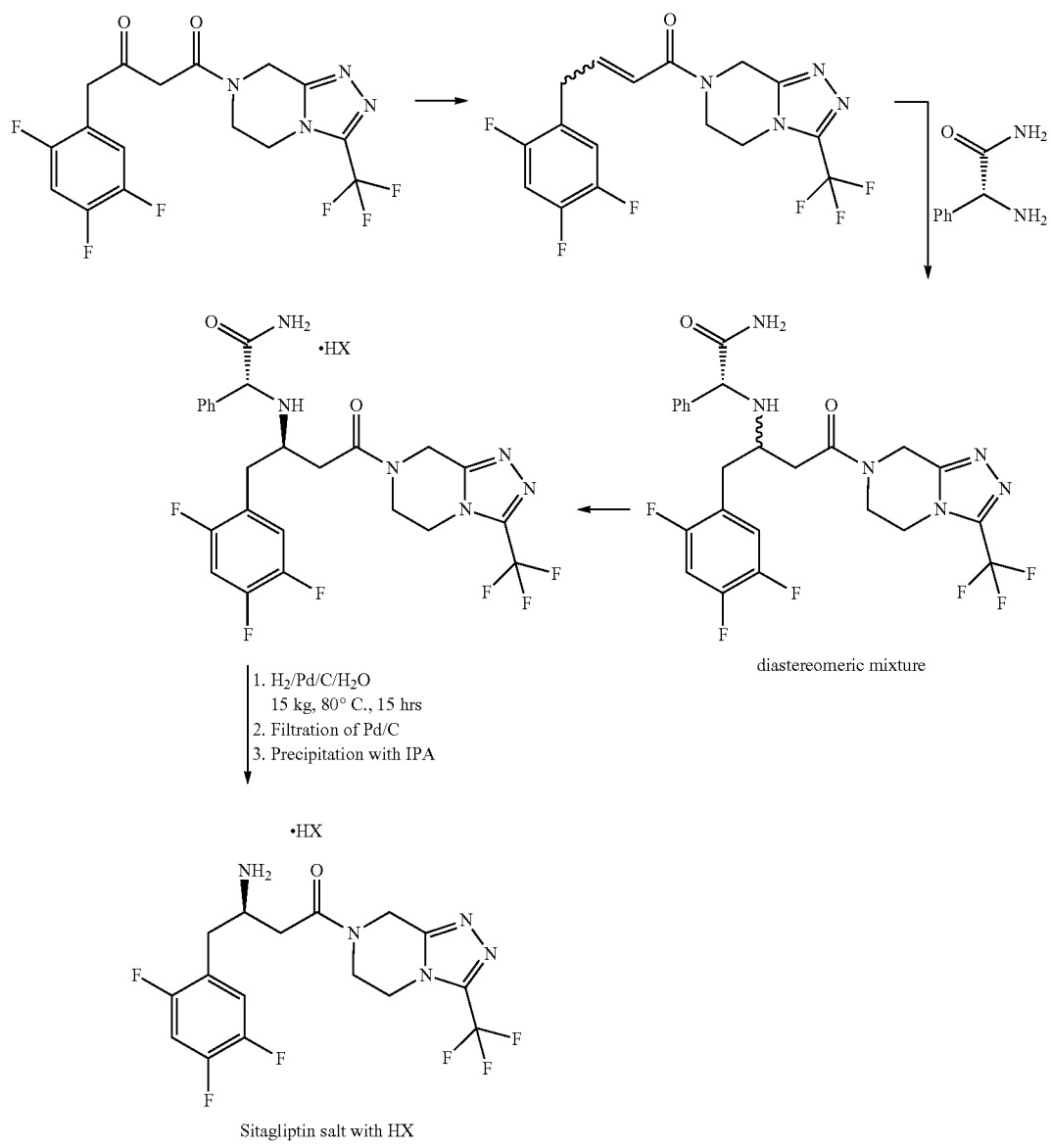
diastereomeric mixture
1. H₂/Pd/C/H₂O
   15 kg, 80° C., 15 hrs
2. Filtration of Pd/C
3. Precipitation with IPA
Sitagliptin salt with HX
wherein HX are as described herein.

Scheme 10
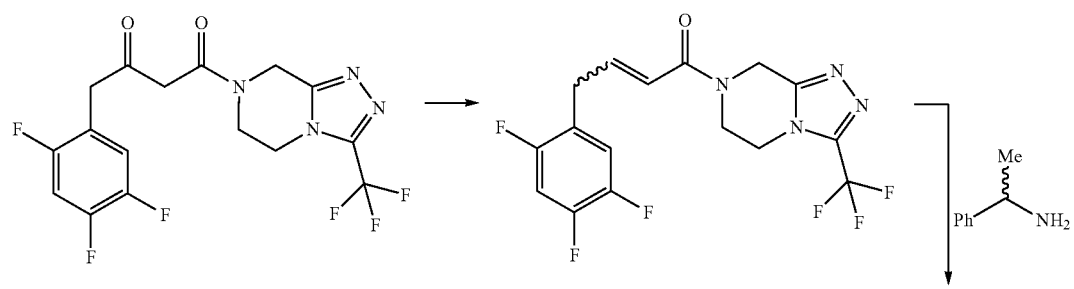
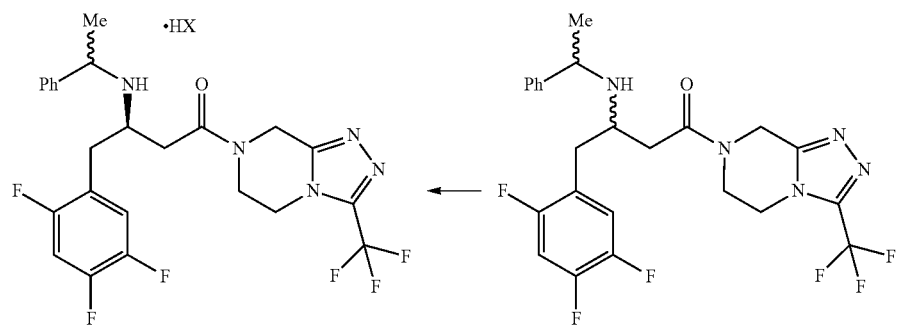
diastereomeric mixture
1. H₂/Pd/C/H₂O
   15 kg, 80° C., 15 hrs
2. Filtration of Pd/C
3. Precipitation with IPA
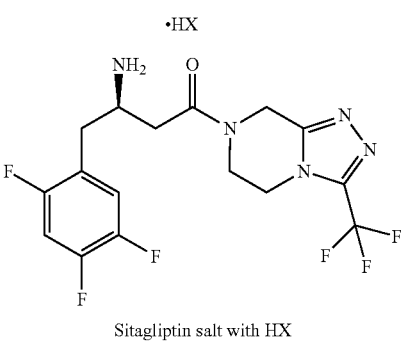
Sitagliptin salt with HX
wherein HX are as described herein.
Scheme 11
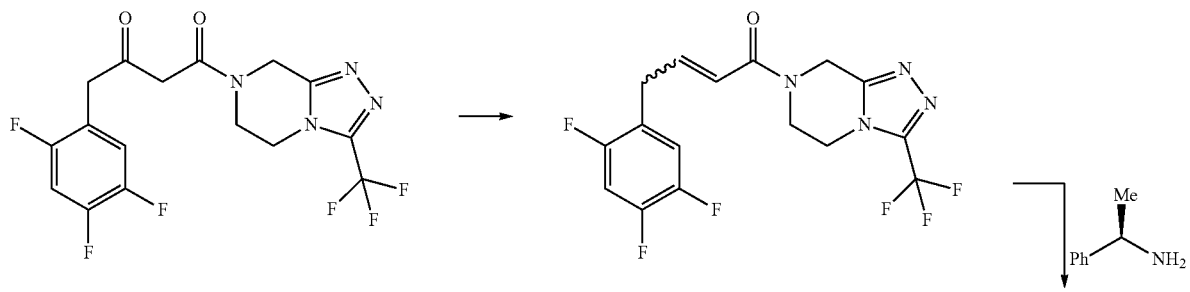

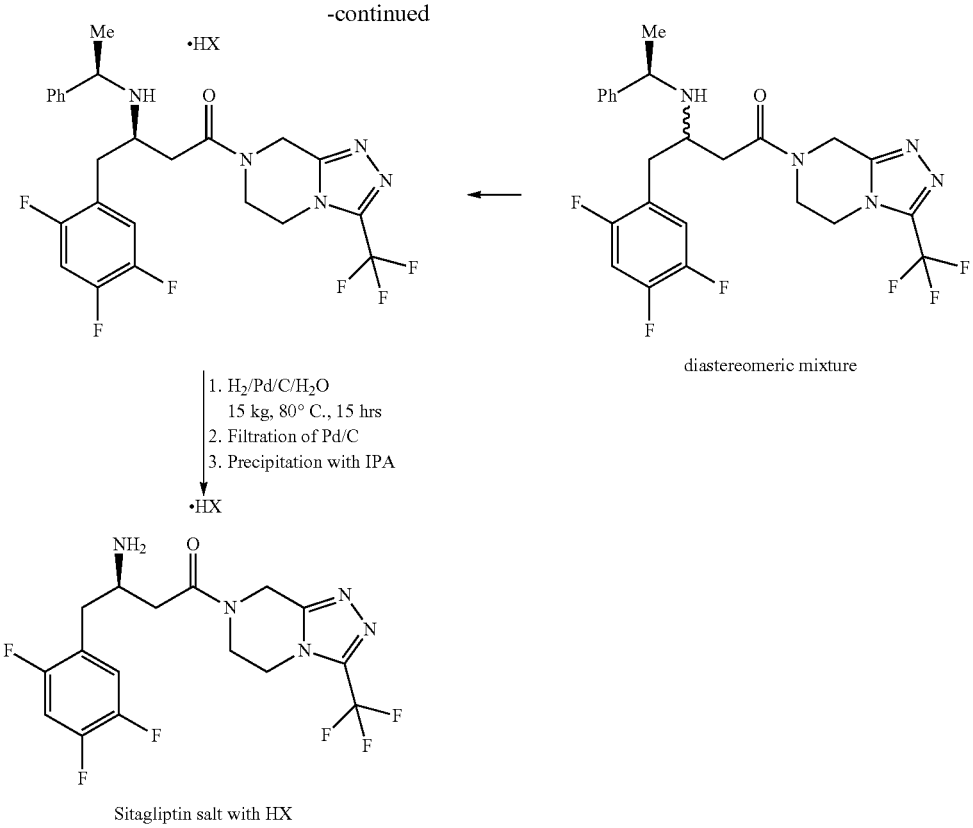
wherein HX are as described herein.
Scheme 12
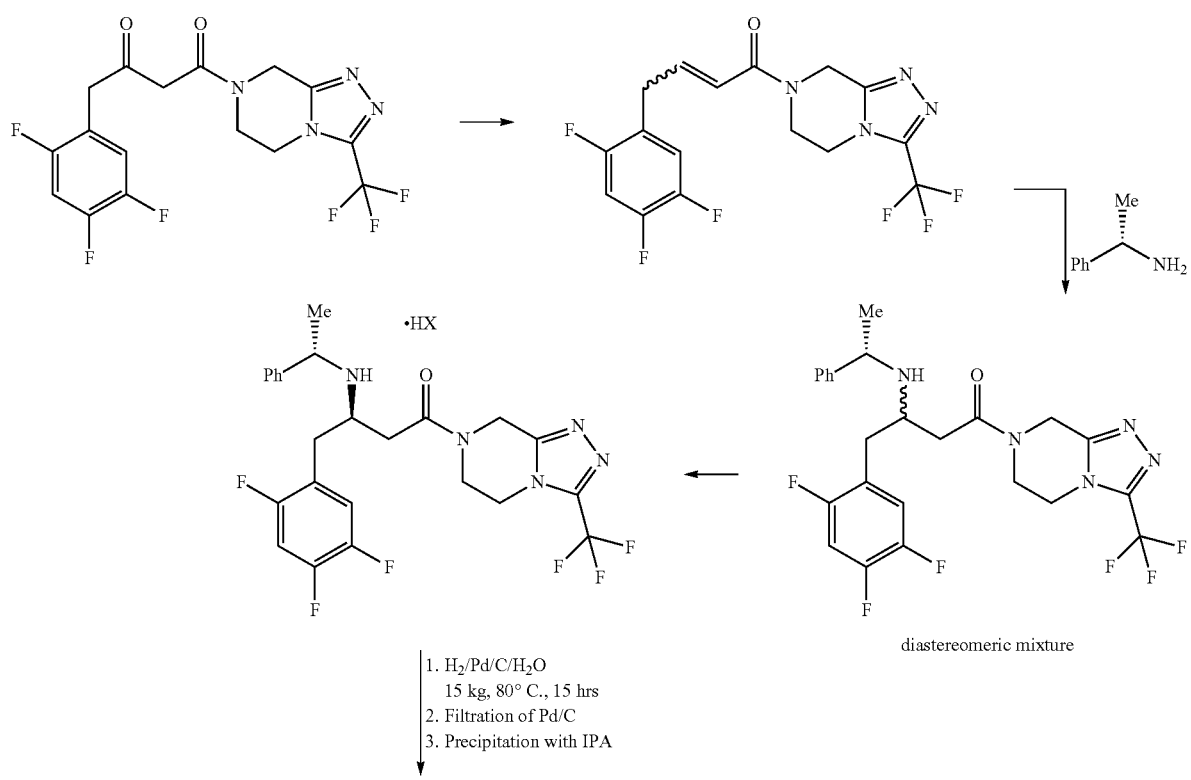

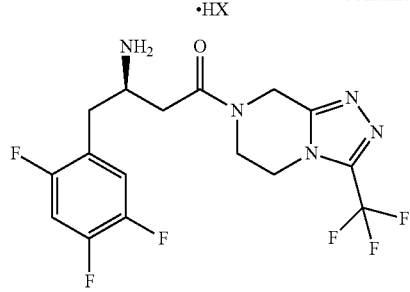

Sitagliptin salt with HX wherein HX are as described herein.

In Schemes 4-14, the reaction of the β-ketoamide to form the enamide, can be carried out by reacting the β-ketoamide compound with hydrogen in the presence of a catalyst and in acidic medium. For example, the reaction can be carried out in acetic acid and in the presence of hydrogen gas, Pd/C and acetic anhydride. Alternately, the reaction can be carried out in the presence of a borane reagent, such as sodium borohydride, and a dehydrating agent, such as pyridinium tosylate.

In Schemes 4-14, the amine addition to the enamide is a Michael addition reaction and it can be carried out under generic Michael addition reaction conditions known to one skilled in the art.

In Schemes 4-14, the purification of the diastereomeric mixture involves a separation of the desired isomer from the mixture and can be carried out by crystallization.

In the Schemes 4-14, the reaction acid salt formation involves reacting the desired isomer isolated by C3 step with an acid HX to form an acid addition salt and HX is as defined herein. For example, HX can be acetic acid or phosphoric acid.

In Schemes 4-14, the final step to form sitagliptin salt involves debenzylation of the acid salt under hydrogenolysis conditions. Such hydrogenolysis conditions can be any hydrogenolysis conditions known to one skilled in the art. For example, the hydrogenolysis can be carried out with hydrogen gas in the presence of a hydrogenolysis catalyst and in a suitable solvent. The catalyst may be Pd/C and the suitable solvent may be water.

In Schemes 4-14, in the final step sitagliptin salt is in a solvate form. For example, sitagliptin salt is a monohydrate of the salt.

EXAMPLES

Example 1

Representative synthesis of compounds of formula II:

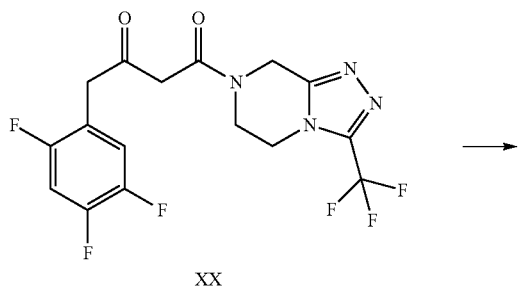

XX

1-[3-(trifluoromethyl)-6,8-dihydro-5H-[1,2,4]triazolo[4,3-a]pyrazin-7-yl]-4-(2,4,5-trifluorophenyl)butane-1,3-dione (XX) is subjected to hydrogenolysis under hydrogen pressure using Pd/C for several hours in acetic acid and in the presence of acetic anhydride. After the completion of reaction (monitored by HPLC), the catalyst is filtered off, the filtrate is diluted with water, followed by the usual workup to afford the desired enamide (II) as a mixture of geometrical isomers.

Example 2

Additional representative synthesis of compounds of formula II:

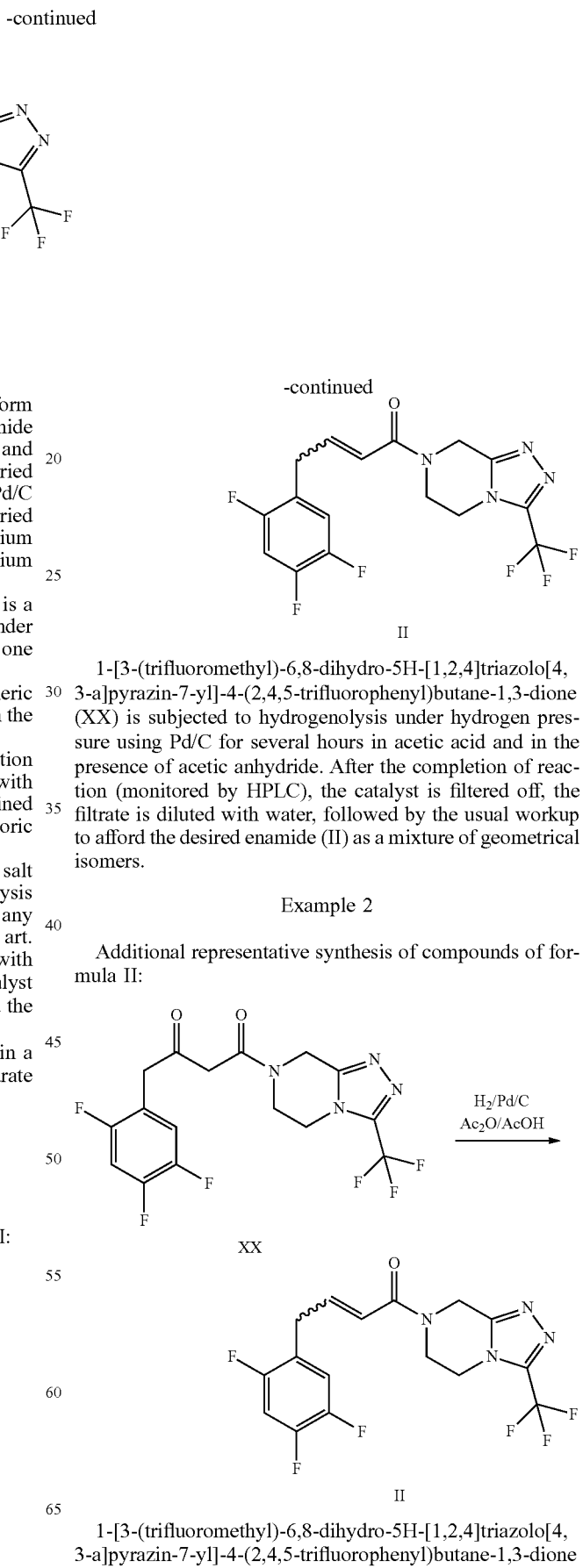

1-[3-(trifluoromethyl)-6,8-dihydro-5H-[1,2,4]triazolo[4,3-a]pyrazin-7-yl]-4-(2,4,5-trifluorophenyl)butane-1,3-dione is subjected to pressure hydrogenation in the presence of acetic anhydride in acetic acid to produce O-acetyl derivative that dehydrates spontaneously to furnish the desired olefin (1-[3-(trifluoromethyl)-6,8-dihydro-5H-[1,2,4]triazolo[4,3-a]pyrazin-7-yl]-4-(2,4,5-trifluorophenyl)but-2-en-1-one as a mixture of E/Z isomers.

Example 3

Representative synthesis of compounds of formula I:

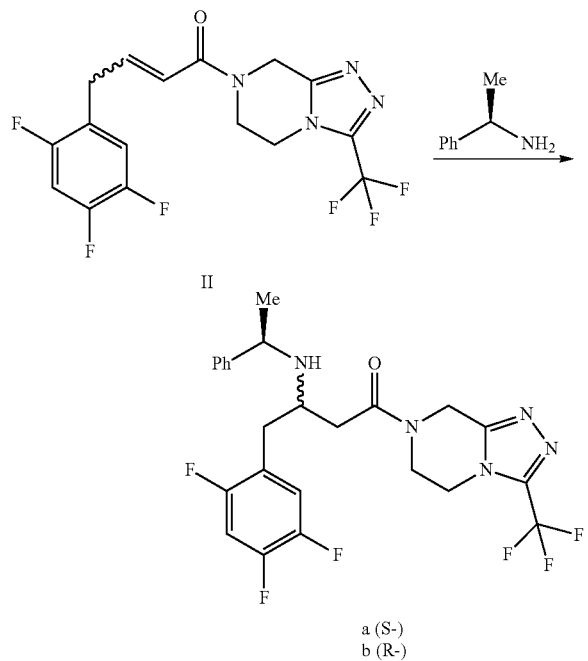

a (S-)
b (R-)

An equimolar methanolic solution of 1-[3-(trifluoromethyl)-6,8-dihydro-5H-[1,2,4]triazolo[4,3-a]pyrazin-7-yl]-4-(2,4,5-trifluorophenyl)but-2-en-1-one and (1R)-1-phenylethanamine is treated with catalytic amount of AcOH and the mixture is stirred at ambient temperature for 24 hours. The desired diastereomer (3R)-3-[[(1R)-1-phenylethyl]amino]-1-[3-(trifluoromethyl)-6,8-dihydro-5H-[1,2,4]triazolo[4,3-a]pyrazin-7-yl]-4-(2,4,5-trifluorophenyl)butan-1-one is crystallized out and further used in the ensuing step.

Example 4

Alternate representative synthesis of compounds of formula I:

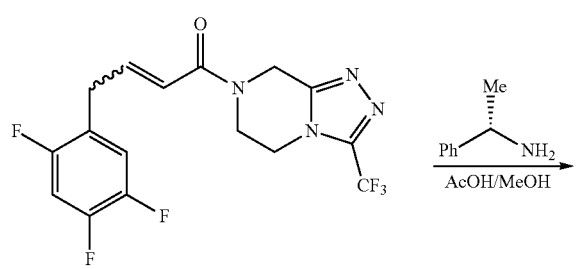

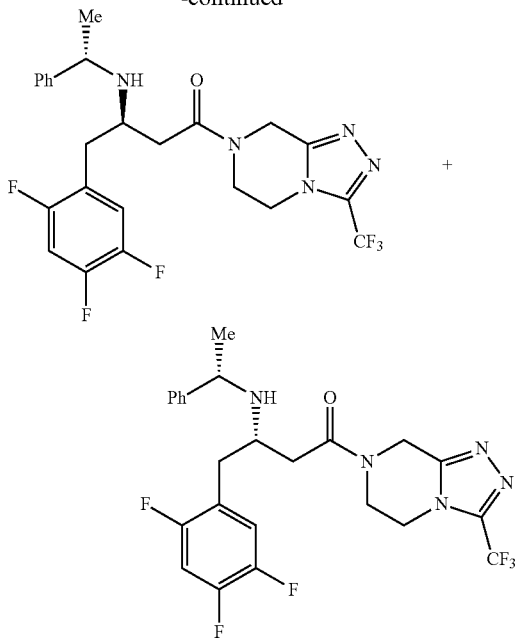

An equimolar methanolic solution of 1-[3-(trifluoromethyl)-6,8-dihydro-5H-[1,2,4]triazolo[4,3-a]pyrazin-7-yl]-4-(2,4,5-trifluorophenyl)but-2-en-1-one and (1S)-1-phenylethanamine is treated with catalytic amount of AcOH and the mixture is stirred at ambient temperature for 24 hours. The desired diastereomer (3R)-3-[[(1S)-1-phenylethyl]amino]-1-[3-(trifluoromethyl)-6,8-dihydro-5H-[1,2,4]triazolo[4,3-a]pyrazin-7-yl]-4-(2,4,5-trifluorophenyl)butan-1-one is crystallized out and further used in the ensuing step.

Example 5

Representative synthesis of compounds of formula X:

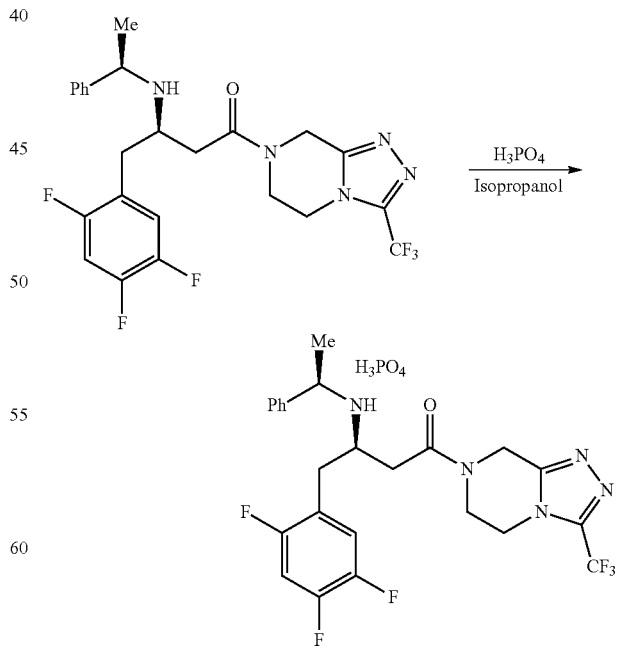

An isopropanol solution of (3R)-3-[[(1R)-1-phenylethyl]amino]-1-[3-(trifluoromethyl)-6,8-dihydro-5H-[1,2,4]triazolo[4,3-a]pyrazin-7-yl]-4-(2,4,5-trifluorophenyl)butan-1- one (Example 3) is treated with molar quantity of $H_3PO_4$ at room temperature and the precipitate is filtered, washed with isopropanol and vacuum dried until constant weight to furnish (3R)-3-[[(1R)-1-phenylethyl]amino]-1-[3-(trifluoromethyl)-6,8-dihydro-5H-[1,2,4]triazolo[4,3-a]pyrazin-7-yl]-4-(2,4,5-trifluorophenyl)butan-1-one, compound with phosphoric acid.

Example 6

Alternate representative synthesis of compounds of formula X:

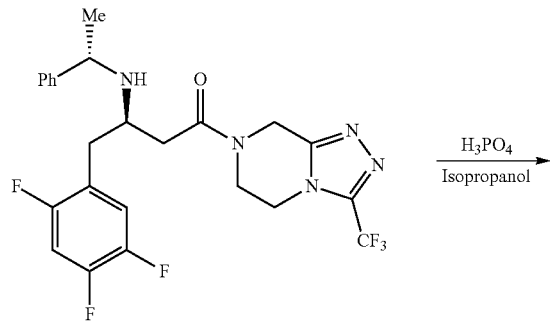

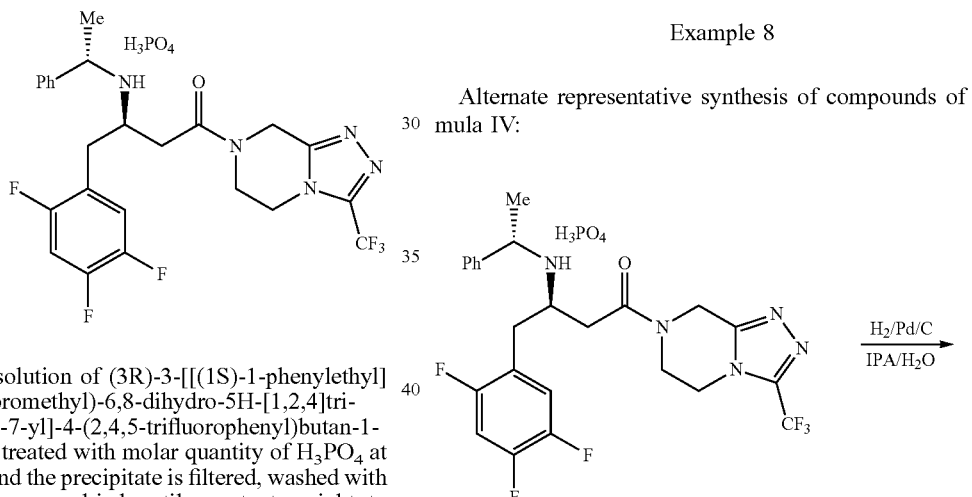

An isopropanol solution of (3R)-3-[[(1S)-1-phenylethyl]amino]-1-[3-(trifluoromethyl)-6,8-dihydro-5H-[1,2,4]triazolo[4,3-a]pyrazin-7-yl]-4-(2,4,5-trifluorophenyl)butan-1-one (Example 4) is treated with molar quantity of $H_3PO_4$ at room temperature and the precipitate is filtered, washed with isopropanol and vacuum dried until constant weight to furnish (3R)-3-[[(1S)-1-phenylethyl]amino]-1-[3-(trifluoromethyl)-6,8-dihydro-5H-[1,2,4]triazolo[4,3-a]pyrazin-7-yl]-4-(2,4,5-trifluorophenyl)butan-1-one, compound with phosphoric acid.

Example 7

Representative synthesis of compounds of formula IV:

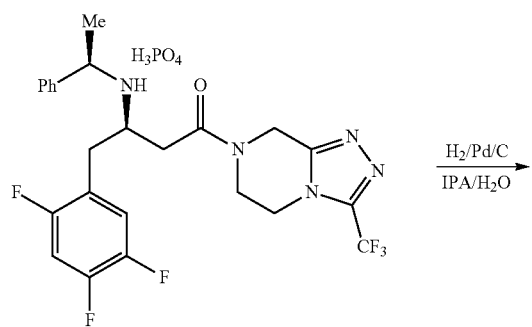

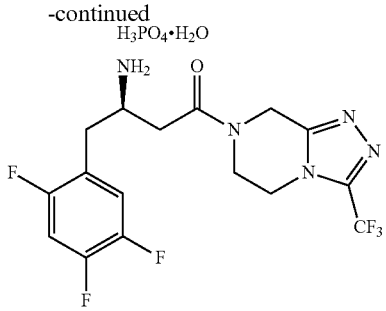

The above phosphoric acid salt from Example 5 in 4:1 mixture of isopropanol/water and 5% Pd/C (10 weight percent) are charged into an autoclave and pressurized to 12 kg with hydrogen. The temperature is slowly raised to 75° C. and the mixture is agitated under pressure for several hours until the hydrogenolysis is complete. Hydrogen gas is ventilated and Pd/C is filtered through a celite bed and the clear filtrate is cooled to 5° C. The white precipitate is filtered and washed with isopropanol and air-dried to obtain sitagliptin phosphate monohydrate.

Example 8

Alternate representative synthesis of compounds of formula IV:

The above phosphoric acid salt from Example 6 in 4:1 mixture of isopropanol/water and 5% Pd/C (10 weight percent) are charged into an autoclave and pressurized to 12 kg with hydrogen. The temperature is slowly raised to 75° C. and the mixture is agitated under pressure for several hours until the hydrogenolysis is complete. Hydrogen gas is ventilated and Pd/C is filtered through a celite bed and the clear filtrate is cooled to 5° C. The white precipitate is filtered and washed with isopropanol and air-dried to obtain sitagliptin phosphate monohydrate.

Example 9

Representative synthesis of compounds of formula XII:

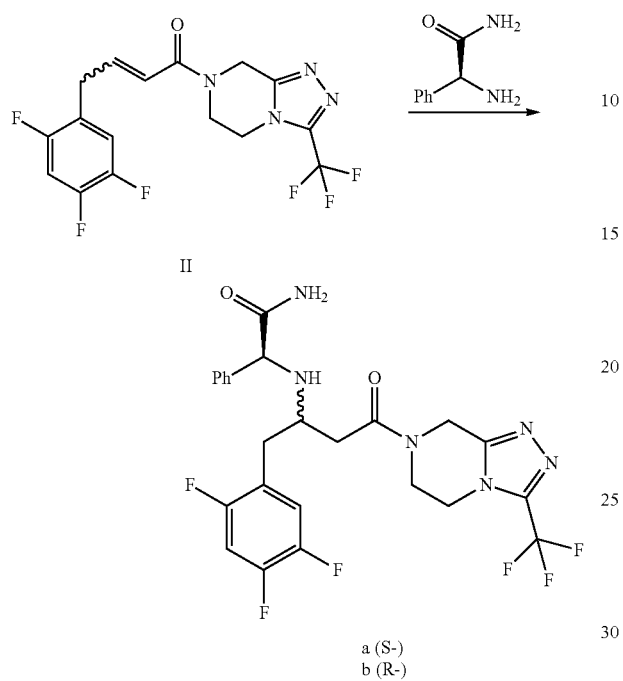

a (S-)
b (R-)

An equimolar methanolic solution of 1-[3-(trifluoromethyl)-6,8-dihydro-5H-[1,2,4]triazolo[4,3-a]pyrazin-7-yl]-4-(2,4,5-trifluorophenyl)but-2-en-1-one and (1R)-1-carboxamidophenylmethanamine is treated with catalytic amount of AcOH and the mixture is stirred at ambient temperature for 24 hours. The desired diastereomer (3R)-3-[[(1R)-1-carboxamidophenylmethyl]amino]-1-[3-(trifluoromethyl)-6,8-dihydro-5H-[1,2,4]triazolo[4,3-a]pyrazin-7-yl]-4-(2,4,5-trifluorophenyl)butan-1-one is crystallized out and further used in the ensuing step.

Example 10

Representative synthesis of compounds of formula XIII:

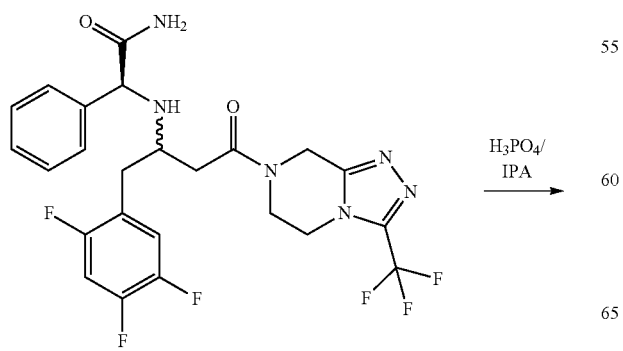

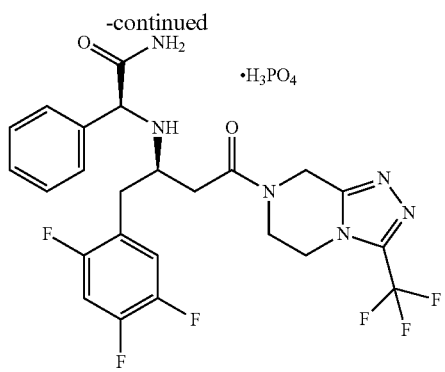

An isopropanol solution of the compound from Example 9 is treated with molar quantity of $H_3PO_4$ at room temperature and the precipitate is filtered, washed with isopropanol and vacuum dried until constant weight to furnish (3R)-3-[[(1R)-1-carboxamido-phenylmethyl]amino]-1-[3-(trifluoromethyl)-6,8-dihydro-5H-[1,2,4]triazolo[4,3-a]pyrazin-7-yl]-4-(2,4,5-trifluorophenyl)butan-1-one, compound with phosphoric acid.

Example 11

Representative synthesis of compounds Sitagliptin or compound of formula IV:

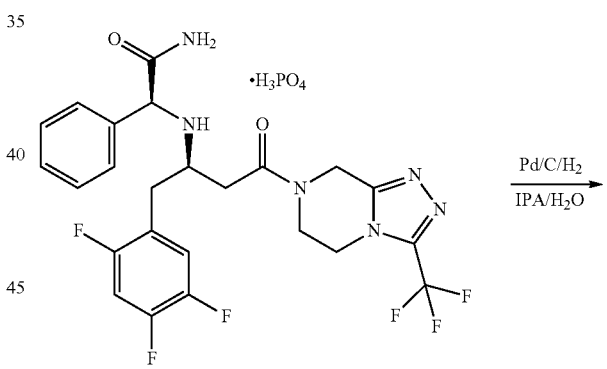

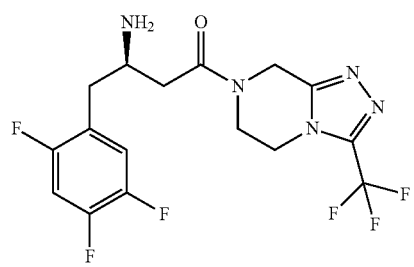

The above phosphoric acid salt from Example 10 in 4:1 mixture of isopropanol/water and 5% Pd/C (10 weight percent) are charged into an autoclave and pressurized to 12 kg with hydrogen. The temperature is slowly raised to 75° C. and the mixture is agitated under pressure for several hours until the hydrogenolysis is complete. Hydrogen gas is ventilated and Pd/C is filtered through a celite bed and the clear filtrate is cooled to 5° C. The white precipitate is filtered and washed with isopropanol and air-dried to obtain sitagliptin phosphate monohydrate.

Example 12

Preparation of an unequal mixture of positional as well as geometric isomers (formula II) composed of (Z/E)-1-[3-(trifluoromethyl)-6,8-dihydro-5H-[1,2,4]triazolo[4,3-a]pyrazin-7-yl]-4-(2,4,5-trifluorophenyl)but-3-en-1-one and (Z/E)-1-[3-(trifluoromethyl)-6,8-dihydro-5H-[1,2,4]triazolo[4,3-a]pyrazin-7-yl]-4-(2,4,5-trifluorophenyl)but-3-en-1-one

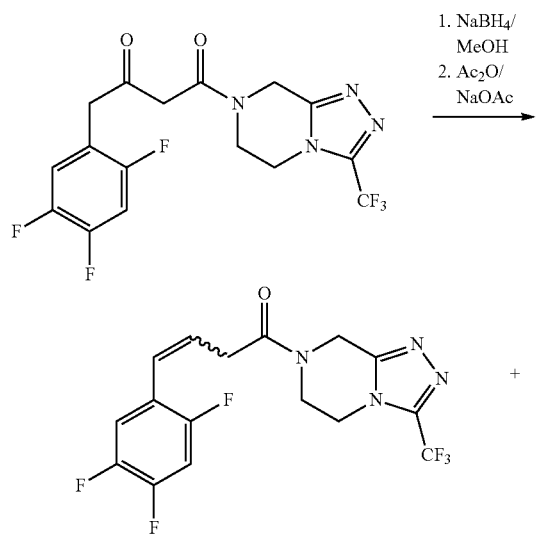

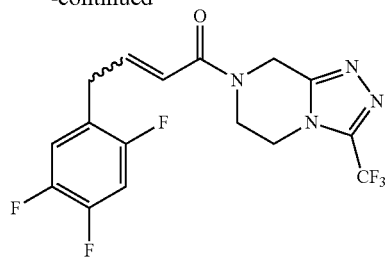

To a cooled (0° C.) solution of 4-phenyl-1-[3-(trifluoromethyl)-6,8-dihydro-5H-[1,2,4]triazolo[4,3-a]pyrazin-7-yl]butane-1,3-dione (100 g, 0.246 mol) in methanol (400 mL) was added $NaBH_4$ (9.32 g, 0.246 mol) slowly during 30 minutes and the mixture was stirred at the same temperature for an additional 1 hour before being quenched with saturated $NH_4Cl$ solution. The white precipitate was filtered off, washed with water and vacuum dried until constant weight to yield the crude carbinol which was further used in the ensuing reaction without further purification.

The crude carbinol obtained above was suspended in toluene (800 mL) and treated successively with sodium acetate (60 g, 0.738 mol) and acetic anhydride (37.64 g, 0.369 mol). The heterogeneous mixture was heated to reflux for 6 hours for complete conversion of the carbinol to the olefin (TLC). The mixture was cooled to 60° C. and was washed successively with water and brine, and the organic layer was gradually cooled to 0° C. to form a precipitate which was filtered, washed with toluene and vacuum dried at 50° C. until constant weight to obtain the title compounds as an unequal mixture of positional (~95:5; non-conjugated: conjugated) and geometric isomers (85 g, 88.6%).

ESI-MS: m/z=391 (M+1). $^1$H NMR ($CDCl_3$): 7.35-7.22 (m, 1H); 6.95-6.80 (m, 1H); 6.60-6.50 (m, 1H); 6.40-6.25 (m, 1H); 5.10-4.95 (m, 2H); 4.30-4.0 (m, 4H); 3.55-3.90 (m, 2H).

Scheme 13

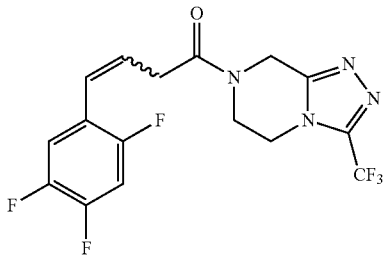

13-Ia

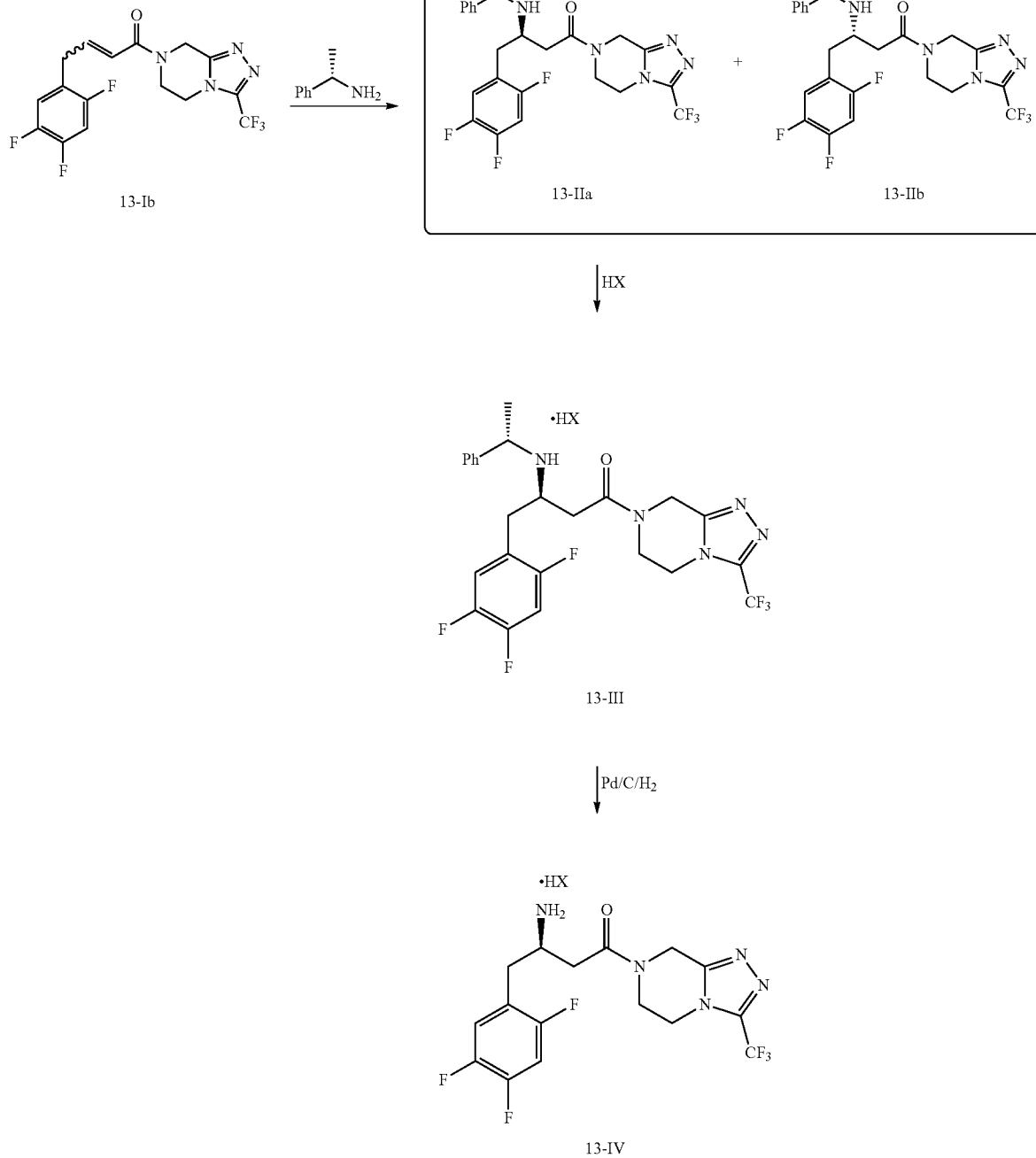

Example 13

(3R)-3-[[(1S)-1-phenylethyl]amino]-1-[3-(trifluoromethyl)-6,8-dihydro-5H-[1,2,4]triazolo[4,3-a]pyrazin-7-yl]-4-(2,4,5-trifluorophenyl)butan-1-one benzene sulfonate The Michael acceptor (13-Ia/Ib) (20 g, 51.28 mmol) was suspended in toluene (100 mL) and was treated successively with (1S)-1-phenylethanamine (12.42 g, 102.56 mmol) and a catalytic amount of benzene sulfonic acid and the mixture was heated at 90° C. for 24 hours. It was then cooled to 50° C. and washed with an aqueous solution of acetic acid (4 g in 50 mL water) followed by brine. The organic layer was heated to 90° C. to which was added benzene sulfonic acid (4.86 g, 30.77 mmol) all at once followed by the seed crystal and the suspension was allowed to gradually cool to ambient temperature. The precipitate was filtered, washed with toluene and vacuum dried at ambient temperature until constant weight to obtain the title compound (13-III, HX=benzenesulfonic acid) (17.16 g, 50%) with a melting range of 130-132° C. Diastereomeric purity by HPLC=99.8%.

Example 14

(3R)-3-[[(1S)-1-phenylethyl]amino]-1-[3-(trifluoromethyl)-6,8-dihydro-5H-[1,2,4]triazolo[4,3-a]pyrazin-7-yl]-4-(2,4,5-trifluorophenyl)butan-1-one oxalate The Michael acceptor (13-Ia/Ib) (20 g, 51.28 mmol) was suspended in toluene (100 mL) and was treated successively with (1S)-1-phenylethanamine (12.42 g, 102.56 mmol) and a catalytic amount of acetic acid and the mixture was heated at 80° C. for 24 hours. It was then cooled to 50° C. and washed successively with an aqueous solution of acetic acid (4 gr in 50 mL water) followed by brine. The organic layer was heated to 80° C. at which was added oxalic acid (2.77 g, 30.77 mmol) all at once followed by the seed crystal and the suspension was allowed to gradually cool to ambient temperature. The white precipitate was filtered, washed with toluene and vacuum dried at ambient temperature until constant weight to obtain the title compound (13-III, HX=oxalic acid) (16.03 g, 52%). M.P. 158-160° C. Diastereomeric purity by HPLC=99.7%.

Example 15

Sitagliptin Phosphate Monohydrate

The oxalate salt obtained above (10 g, 16.63 mmol) was charged into an autoclave and suspended in isopropanol (60 mL) to which was added 5% Pd/C (1 g, 10 weight percent to the substrate). The vessel was pressurized to 12 kg with hydrogen gas and agitated for 3 hours at 70° C. HPLC analysis indicated complete hydrogenolysis. Hydrogen gas was vented out slowly at the same temperature and the catalyst filtered out. The filtrate was heated to 80° C. and was treated with orthophosphoric acid (17.47 mmol, 50% aqueous solution). The mixture was allowed to cool to ambient temperature, filtered, washed with isopropanol (20 mL) and vacuum dried at 50° C. until constant weight to yield sitagliptin phosphate monohydrate (13-IV monohydrate, HX=phosphoric acid) (8.41 g, 97%) with 99.9% enantiomeric purity.

Example 16

(3R)-3-[[(1S)-1-phenylethyl]amino]-1-[3-(trifluoromethyl)-6,8-dihydro-5H-[1,2,4]triazolo[4,3-a]pyrazin-7-yl]-4-(2,4,5-trifluorophenyl)butan-1-one phosphate A suspension of the Michael acceptor (13-Ia/Ib) (40 g, 102.56 mmol) and (1S)-1-phenylethanamine (24.84 g, 205.12 mmol) and a catalytic amount of racemic lactic acid was heated at 90° C. for 30 hours. Toluene (300 mL) was added at the same temperature and the solution was cooled to 50° C. Excess chiral auxiliary was washed with an aqueous solution of acetic acid (8 gr in 100 mL water) followed by brine. The organic layer was heated to 80° C. to which was added 85% orthophosphoric acid (56.5 mmol) all at once followed by the seed crystal and the suspension was allowed to gradually cool to ambient temperature. The white precipitate was filtered, washed with toluene and vacuum dried at ambient temperature until constant weight to obtain the title compound (13-III, HX=phosphoric acid) (31.87 g, 51%). HPLC indicated 99.8% diastereomeric purity.

$^1$H NMR (DMSO-d6): 7.5-7.05 (m, 7H); 5.1-4.7 (m, 2H); 4.2-3.7 (m, 5H); 3.15-2.30 (m, 5H); 1.25-1.10 (m, 3H).

Example 17

Sitagliptin Phosphate Monohydrate-Alternate Synthesis

The phosphate salt obtained above (10 g, 16.47 mmol) was suspended in acetic acid (80 mL) and the mixture was charged into an autoclave. The vessel was pressurized with hydrogen to 12 kg and heated at 60° C. for 8 hours. HPLC analysis indicated complete hydrogenolysis of the starting material. Hydrogen gas was then slowly vented out at the same temperature and the solids filtered, washed with acetic acid (20 mL). The filtrate was concentrated under vacuum to dryness and the residue was dissolved in isopropanol (60 mL), heated to 75° C. and treated with water (1 mL). The clear solution was gradually allowed to cool to ambient temperature during 4 hours. The precipitate was filtered, washed with isopropanol (20 mL) and vacuum dried at 50° C. until constant weight to obtain sitagliptin phosphate monohydrate (13-IV monohydrate, HX=phosphoric acid) (8.24 g, 96%) with 99.9% enantiomeric purity.

Scheme 14

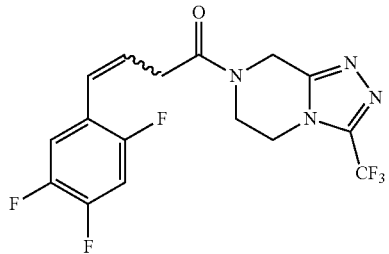

14-Ib

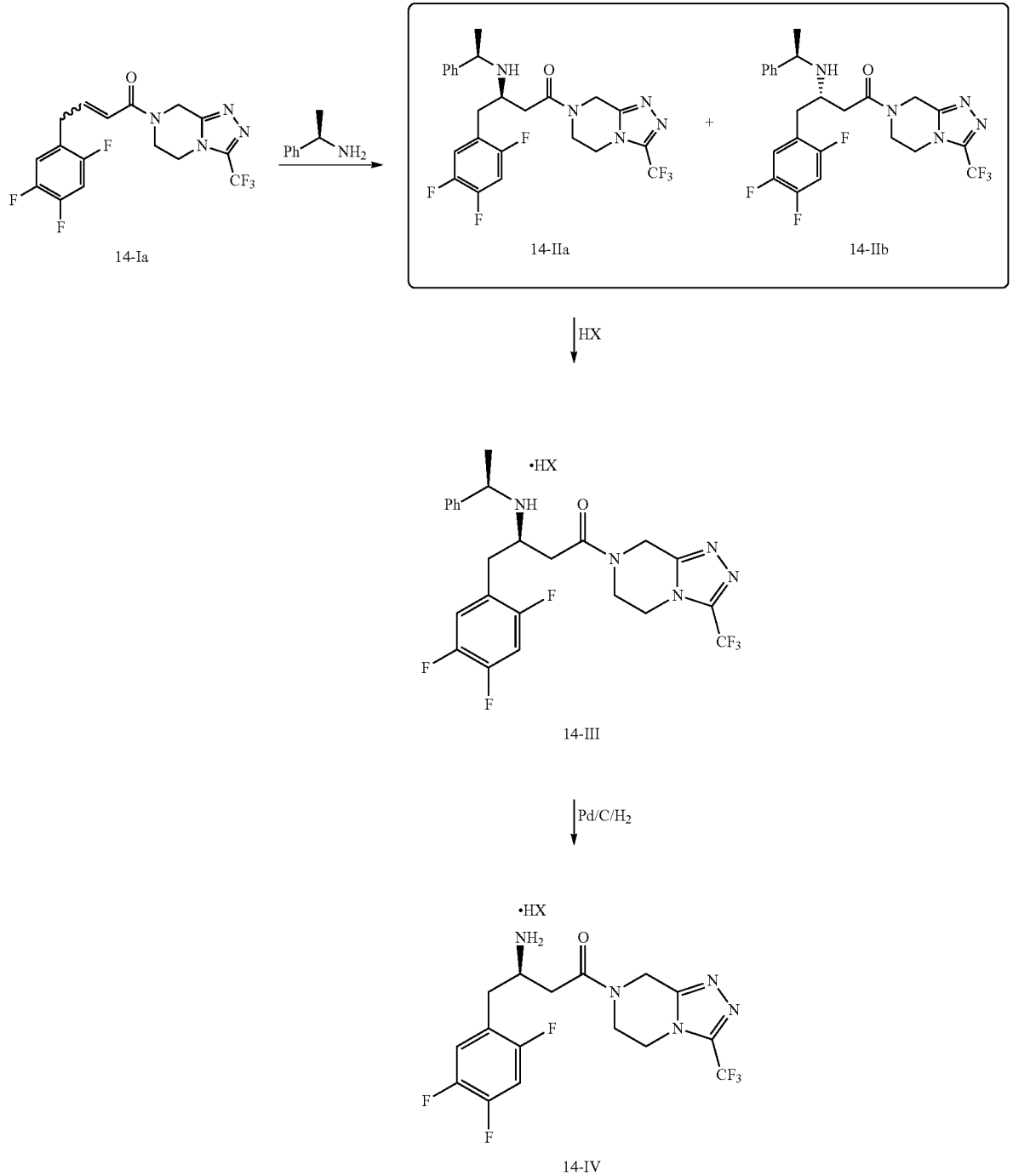

Example 18

(3R)-3-[[(1R)-1-phenylethyl]amino]-1-[3-(trifluoromethyl)-6,8-dihydro-5H-[1,2,4]triazolo[4,3-a]pyrazin-7-yl]-4-(2,4,5-trifluorophenyl)butan-1-one phosphate

A suspension of the Michael acceptor (14-Ia/Ib) (40 g, 102.56 mmol) and (1R)-1-phenylethanamine (24.84 g, 205.12 mmol) and a catalytic amount of racemic lactic acid was heated at 90° C. for 30 hours. Toluene (300 mL) was added at the same temperature and the solution was cooled to 50° C. The excess chiral auxiliary was washed with an aqueous solution of acetic acid (8 gr in 100 mL water) followed by brine. The organic layer was heated to 80° C. to which was added 85% orthophosphoric acid (51.28 mmol) all at once and the suspension was allowed to gradually cool to ambient temperature. The white precipitate was filtered, washed with toluene and vacuum dried at ambient temperature until constant weight to obtain the title compound (14-111, HX=phosphoric acid) (28.12 g, 45%). M.p. 178-183° C.

¹H NMR (DMSO-d6): 7.45-7.0 (m, 7H); 5.05-4.75 (m, 2H); 4.15-3.80 (m, 5H); 3.0-2.45 (m, 5H); 1.25-1.10 (m, 3H).

Example 19

Sitagliptin Phosphate Monohydrate

The phosphate salt obtained above (10 g, 16.47 mmol) was suspended in acetic acid (80 mL) and the mixture was charged into an autoclave. The vessel was pressurized with hydrogen to 12 kg and heated at 60° C. for 8 hours. HPLC analysis indicated complete hydrogenolysis of the starting material. Hydrogen gas was then slowly vented out at the same temperature and the solids filtered, washed with acetic acid (20 mL). The filtrate was concentrated under vacuum to dryness and the residue was dissolved in isopropanol (60 mL), heated to 75° C. and treated with water (1 mL). The clear solution was gradually allowed to cool to ambient temperature during 4 hours. The precipitate was filtered, washed with isopropanol (20 mL) and vacuum dried at 50° C. until constant weight to obtain sitagliptin phosphate monohydrate (14-IV monohydrate, HX=phosphoric acid) (8.33 g, 97%) with 99.9% enantiomeric purity.

Exemplary Compounds of the Invention

The following compounds and stereoisomers, or salts thereof have been or can be prepared according to the methods of the invention. The calculated molecular weight of the representative compounds are given in Table 1 below.

TABLE 1

Exemplary Compounds of the Invention

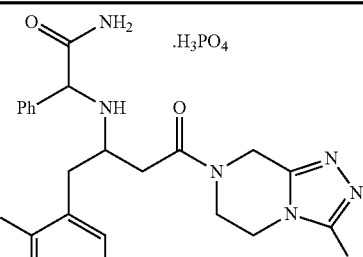

*Ph in unsubstituted phenyl;
**and stereoisomers thereof.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, all enantiomers associated with the chiral center are encompassed by the chemical structure.

What is claimed is:

1. A process for the preparation of an intermediate compound of formula I:

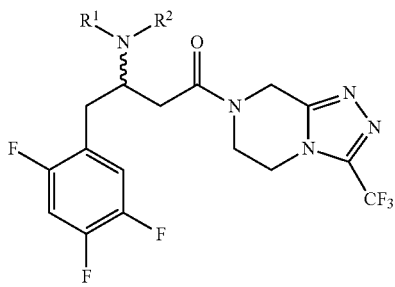

or a salt thereof; wherein
each $R^1$ and $R^2$ is independently H, substituted or unsubstituted alkyl, substituted or unsubstituted alkoxy, substituted or unsubstituted aryl, substituted or unsubstituted aryloxy, substituted or unsubstituted aralkyl, substituted or unsubstituted heterocycloalkyl, or substituted or unsubstituted cycloalkyl, —C(O)—$R^3$, —C(O)—$OR^3$, —O—C(O)—$R^3$, —S(O)$_2$—$R^3$, —Si($R^3$)$_3$, and —O—Si($R^3$)$_3$; each $R^3$ is independently selected from substituted or unsubstituted alkyl, substituted or unsubstituted benzyl, substituted or unsubstituted cycloalkyl, substituted or unsubstituted aryl, and substituted or unsubstituted heteroaryl;

or $R^1$ and $R^2$ are joined together to form a heterocycle; and the wavy bond represents that the compound is in R—, S— or racemic form;

wherein the process comprises the steps of:

A1) providing an intermediate compound of formula II:

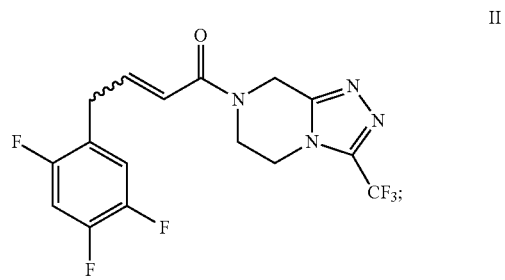 [SMILES: O=C(C=CCc1cc(F)c(F)cc1F)N1CCn2c(nnc2C(F)(F)F)C1]

A2) reacting the intermediate compound of formula II with a Michael donor of formula III:

wherein $R^1$ and $R^2$ are as described for formula I; to obtain the intermediate compound of formula I.

2. The process of claim 1, wherein each $R^1$ and $R^2$ is H.

3. The process of claim 1, wherein the Michael donor is selected from ammonia, dimethylamine, t-butylcarbamate, O-methylhydroxylamine, benzylamine, p-methoxybenzylamine, 3,4-dimethoxybenzylamine, p-methoxyaniline, tosylamine, benzylcarbamate, dibenzylamine, naphthylamine, O-benzylhydroxylamine, O-phenylhydroxylamine, benzhydrylamine, methylphenyl-amine, N-methylbenzylamine, N-benzyl-1-phenethylamine, hexamethyldisilazane, 1,1,3,3-tetramethyl-1,3-diphenylsilazane, O-trimethylsilylhydroxylamine, (S)-1-(naphth-2-yl)ethylamine, (R)-1-(naphth-2-yl)ethylamine, and N,O-bis(trimethylsilyl)hydroxylamine.

4. The process of claim 1, wherein the step A2) occurs in a protic solvent.

5. The process of claim 1, wherein the step A2) occurs in a protic solvent selected from the group consisting of methanol, ethanol, isopropyl alcohol, t-butanol, trifluoroethanol, hexafluoro-2-propanol, amyl alcohol, and combinations thereof.

6. The process of claim 1, wherein the step A2) occurs at about 20° C. to 80° C.

7. The process of claim 1, wherein the step A2) occurs in the presence of an acid.

* * * * *